(12) United States Patent
Nakamura

(10) Patent No.: US 6,545,141 B1
(45) Date of Patent: Apr. 8, 2003

(54) BRAIN-SPECIFIC ADAPTER MOLECULE, GENE THEREOF, AND ANTIBODY THERETO

(75) Inventor: Takeshi Nakamura, Yokohama (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 0 days.

(21) Appl. No.: 09/433,353

(22) Filed: Nov. 4, 1999

Related U.S. Application Data

(62) Division of application No. 08/729,416, filed on Oct. 11, 1996, now Pat. No. 5,795,620.

(30) Foreign Application Priority Data

| Oct. 13, 1995 | (JP) | ............................................. | 7-265988 |
| Dec. 12, 1995 | (JP) | ............................................. | 7-323069 |
| Feb. 29, 1996 | (JP) | ............................................. | 8-069265 |
| Jul. 24, 1996 | (JP) | ............................................. | 8-212973 |

(51) Int. Cl.[7] ........................ C07H 21/02; C07H 21/04; C12P 21/06; C12N 15/00
(52) U.S. Cl. .................. 536/23.5; 435/69.1; 435/320.1; 536/23.1
(58) Field of Search ............................ 435/69.1, 320.1, 435/325; 530/350; 536/23.1, 23.5

(56) References Cited

PUBLICATIONS

Nakamura, T. et al., N–Shc: A neural–specific adapter molecule that mediates signaling from neurotrophin–Trk to Ras–MAPK pathway, Oncogene, 13 (6). 1996 1111–1112.
Pelicci, G. et al., A family of Shc related protein with conserved PTB, CH1 and SH2 regions, Oncogene, 13 (3) 1996 633–641.
Rudinger, "Peptide Hormones", (ed. Parsons), University Park Press, Baltimore, pp. 107, 1976.
Salgaller et al., "Cancer Immunology Immunother.", vol. 39, pp. 105–116, 1994.
Pelicci et al., A Novel Transforming Protein (SHC) with an SH2 Domain Is Implicated in Mitogenic Signal Transduction, Cell, vol. 70, 93–104, Jul. 10, 1992.
Pelicci et al., Constitutive phosphorylation of Shc proteins in human tumors, Oncogene (1995) 11, 899–907.
Obermeier et al., Neuronal differentiation signals are controlled by nerve growth factor receptor/Trk binding sites for SHC and PLC, The EMBO Journal, vol. 13, No. 7, pp. 1585–1590, 1994.
Blaikie et al., A Region in Shc distinct from the SH2 domain can bind Tyrosine–Phosphorylated growth factor receptors, J. Biol. Chem, Dec. 23, 1994 269 (51).
Pawson, T., Protein Modules and signalling networks, Nature, Feb. 16, 1995, 373 (6515) P573–80.
O'Bryan J. P. et al., A mammalian adapter protein with conserved Src homology 2 and phosphotyrosine–binding domains is related to Shc and is specifically expressed in the brain, Proceedings of the Nat'l Acad. of Sci. of the U.S. of A., 93 (7). 1996 2729–2734.

*Primary Examiner*—John Ulm
*Assistant Examiner*—Olga N. Chernyshev
(74) *Attorney, Agent, or Firm*—McDermott, Will & Emery

(57) ABSTRACT

A novel brain-specific adapter molecule, its gene, an antibody to it, and a method of utilizing the antibody are provided. This invention screened a normalized cDNA library using mRNA derived from the human cerebrum, isolated a gene encoding a novel factor, FC99 protein, involved in the signaling pathways in neurons of the brain, and clarified its base sequence as well as a protein encoded by the gene. The invention also isolated from a rat brain-derived cDNA library a gene encoding rat FC99 protein, and clarified its base sequence as well as a protein encoded by the gene. The invention further produced an antibody to the protein, and measured tyrosine kinase activity in a cell by use of the antibody.

5 Claims, 5 Drawing Sheets

FC99: LGPGVTYVVKYLGCIEVLRSMRSLDFESTRTQITREAISRVCEAVPGAK   76
Shc:  MGPGVSYLVRYMGCVEVLQSMRALDFNTRTQVTREAISLVCEAVPGAK   93

FC99: GAFKKRKPPSKMLSSILGKSNLQFAGMSISLTISTASLNLRTPDSKQI    124
Shc:  GATRRRKPCSRPLSSILGRSNLKFAGMSIPITLVSTSSLNLMAADCKQI    141

FC99: IANHHMRSISFASGGDPDTDYVAYVAKDPVNRRACHILECCDGLAQD      172
Shc:  IANHHMQSISFASGGDPDTAEYVAYVAKDPVNQRACHILECPEGLAQD      189

FC99: VIGSIGQAFELRFKQYLQCP                                  192
Shc:  VISTIGQAFELRFKQYLRNP                                  209
```

B

```
FC99: WYQGEMSRKEAEGLLEKDGDFLVRKSTTNPGSFVLTGMHNGAKHLLL     426
Shc:  WFHGKLSRREAEALLQLNGDFLVRESTTTPGQYVLTGLQSGQPKHLLL    425

FC99: VDPEGTIRTKDRVFDSISHLINHLESSLPIVSAGSELCLQQPVERKQ     474
Shc:  VDPEGVVRTKDHRFESVSHLISYHMDNHLPIISAGSELCLQQPVERKL    473
```

় # BRAIN-SPECIFIC ADAPTER MOLECULE, GENE THEREOF, AND ANTIBODY THERETO

This is a division of application Ser. No. 08/729,416, filed Oct. 11, 1996 now U.S. Pat. No. 5,795,620.

BACKGROUND OF THE INVENTION

1. Field of the Invention

This invention relates to a novel brain-specific adapter molecule, its gene, and antibodies to it.

2. Related Background Art

Nerve growth factor (NGF) is known to mainly stimulate the survival and growth of neurons of the brain and maintain the neuronal network through these activities. Neurons of the Meynert's basal ganglia, for example, integrate information from the lower regions of the cerebrum, and constantly send control signals to the cerebral cortex. These neurons receive NGF biosynthesized by neurons of the cerebral cortex, and sustain their survival (Thoenen, Trend NeuroSci., 14, 165–170, 1991, or Hatanaka, H., Cell Engineering, 9, 866–876, 1990).

Based on these findings, NGF is considered to have a high possibility for clinical use in the treatment of various neurological diseases, including recessive ones (e.g., dementia of the Alzheimer type and Parkinson's disease). Orthon et al. (J. Neural Transm. Park. Dement. Sect., 4, 79–95, 1992) have reported clinical use of NGF in patients with Alzheimer's dementia.

NGF actually transmits necessary signals into cells through NGF receptors, and studies of the pathways for the signals are under way (for example, Heumann, Current opinion in Neurobiology, 4, 668–679, 1994). Findings to be obtained through these studies are expected to serve for the direct clinical use of NGF in treating neurological diseases. In the diagnosis and treatment of cancer which abnormalities in growth factors similarly take a great part in, the achievements of researches on the signaling pathways of growth factors have reached the level of clinical application (Nikkei Biotechnology, 8–28, 2, 1995).

SUMMARY OF THE INVENTION

An object of the present invention is to search for and isolate a novel factor involved in the signaling pathways in neurons of the brain (e.g., the signaling pathways within the neurons NGF acts on).

Another object of the invention is to provide means of measuring tyrosine kinase activity in a cell or tissue by use of the novel factor (FC99 protein), the gene (FC99 gene) encoding it, and antibodies to it claimed in the invention.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

FIG. 1 is a view showing a comparison of the amino acid sequences of FC99 and Shc in the PTB domain (upper side A) (SEQ ID NO: 21–22) and the SH2 domain (bottom side B) (SEQ ID NO: 23–24), in which the numeral on the right of the row denotes how many residues in FC99 and Shc are present until the amino acid reside located at the end of the row. For FC99, the numeral shows the position in the amino acid sequence described as SEQ ID NO: 1 in the Sequence Listing;

DESCRIPTION OF THE PREFERRED EMBODIMENTS

We have conducted extensive studies to attain the aforementioned objects, and found that these objects can be attained by screening from a normalized cDNA library using human cerebrum-derived mRNA (prepared in accordance with the method of Sasaki et al., DNA Research 1, 91–96, 1994). This article is hereby incorporated by reference.

That is, we have succeeded in isolating a gene (hereinafter referred to as FC99 gene or N-Shc gene) encoding a polypeptide having two specific domains (PTB domain as in van derGeer et al., Trends Biol. Sci., 20, 277–280, 1995, and SH2 domain as in Pawson, Nature, 373, 573–580, 1995) which are known to recognize phosphorylated tyrosine (its biochemical mechanisms are described, for example, in Heumann: Current opinion in Neurobiology, 4, 668–679, 1994, or Pawson: Nature, 373, 573–580, 1995) known to work as a signal molecule in the signaling pathways in neurons of the brain (e.g., the signaling pathways in neurons where NGF acts).

Figure 2:
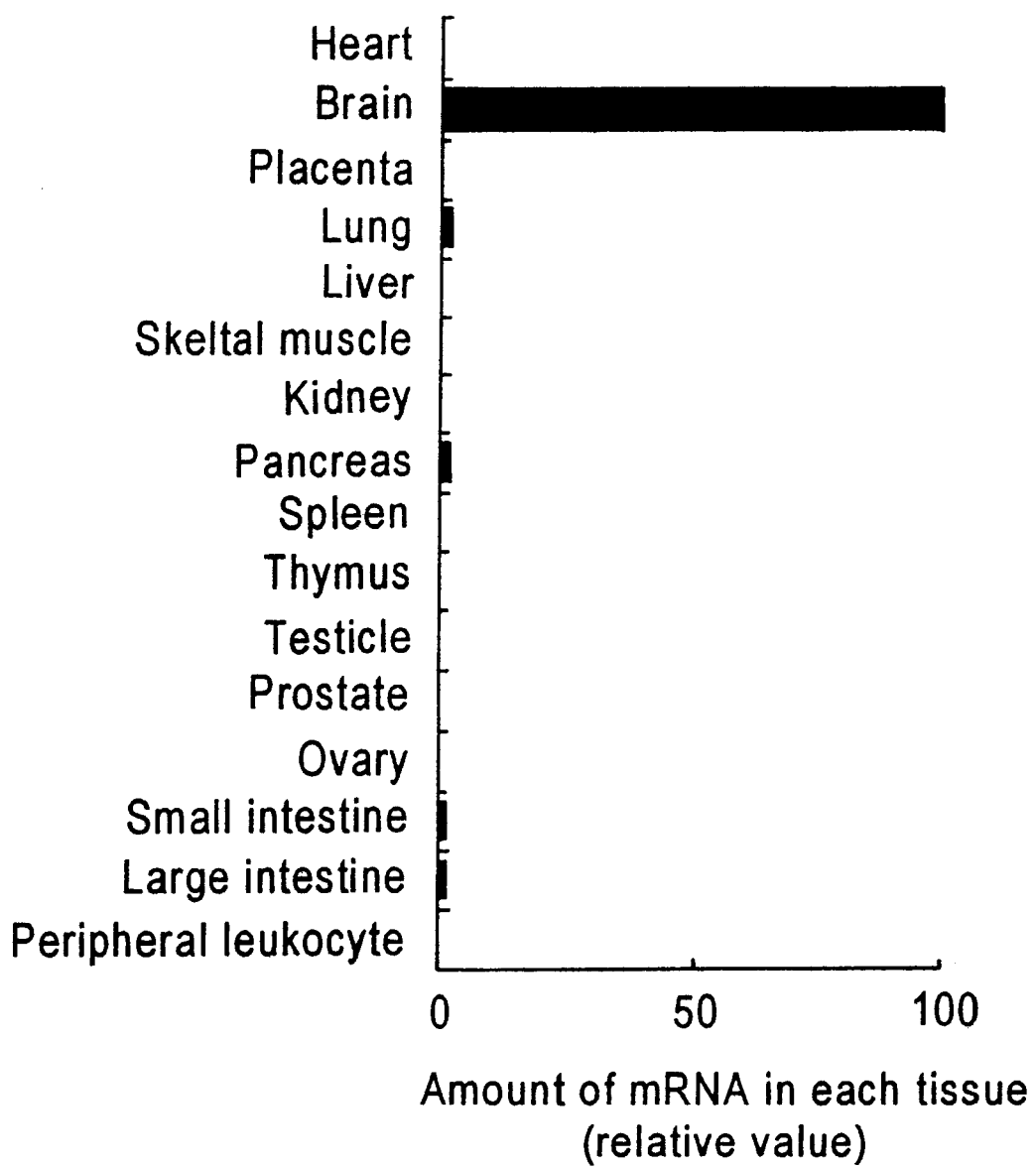
FIG. 2 is a chart showing the amounts of FC99 mRNA expressed in 16 kinds of tissues, with the amount of the mRNA in the brain being designated as 100, and those in the other tissues being relative amounts to it.

We have also clarified that the expression of the FC99 gene is specific for the brain among the 16 tissues investigated (see FIG. 2).

We have further made it clear that the sequence of the resulting FC99 is very similar to Shc (Pelicci et al., Cell, 70, 93–104, 1992), known as an adapter molecule in intracellular signaling pathways, in terms of the amino acid sequences of the PTB domain and the SH2 domain (see FIG. 1).

A comparison of the FC99 obtained in the present invention with the Shc has shown that a tyrosine residue which undergoes phosphorylation (Shc has been shown to bind Grb2, another adapter molecule, via this phosphorylated tyrosine; van der Geer et al., Current Biology, 5, 404–412, 1995), indispensable for Shc to act as an adapter molecule in the intracellular signaling pathways, is preserved in FC99.

As described above, the FC99 protein identified in the present invention is presumed to function as an adapter molecule in phosphorylated tyrosine-mediated intracellular signaling pathways. Thus, the FC99 protein obtained in the present invention and its genetic information can be applied as tools for study of the intracellular signaling pathways, as therapeutic methods or agents for diseases involving abnormalities in the intracellular signaling pathways, and as testing methods or diagnostic reagents for the diseases.

More particularly, the invention relates to polypeptide (1) containing in the molecule at least an amino acid sequence described as SEQ ID NO: 1 in the Sequence Listing.

The invention also relates to polynucleotide (2) containing in the molecule at least a base sequence described as SEQ ID NO: 2 in the Sequence Listing.

The invention also relates to polypeptide (3) containing in the molecule at least an amino acid sequence described as SEQ ID NO: 7 in the Sequence Listing.

The invention also relates to polynucleotide (4) containing in the molecule at least a base sequence described as SEQ ID NO: 8 in the Sequence Listing.

The invention also relates to polypeptide (5) containing in the molecule at least an amino acid sequence described as SEQ ID NO: 3 in the Sequence Listing.

The invention also relates to polynucleotide (6) containing in the molecule at least a base sequence described as SEQ ID NO: 4 in the Sequence Listing.

The invention also relates to polypeptide (7) containing in the molecule at least an amino acid sequence described as SEQ ID NO: 5 in the Sequence Listing.

The invention also relates to polynucleotide (8) containing in the molecule at least a base sequence described as SEQ ID NO: 6 in the Sequence Listing.

The invention also relates to polypeptide (9) containing in the molecule at least both of an amino acid sequence described as SEQ ID NO: 3 in the Sequence Listing and an amino acid sequence described as SEQ ID NO: 5 in the Sequence Listing.

The invention also relates to polynucleotide (10) containing in the molecule at least both of a base sequence described as SEQ ID NO: 4 in the Sequence Listing and a base sequence described as SEQ ID NO: 6 in the Sequence Listing.

The invention also relates to polypeptide (11) containing the amino acid sequence of the polypeptide (1), (3), (5), (7) or (9) that has undergone spontaneous or induced mutation, and having the ability to bind a polypeptide containing a phosphorylated tyrosine residue.

The invention also relates to polynucleotide (12) encoding polypeptide (11).

The invention also relates to polynucleotide (13) having all or part of the sequence of the antisense strand of the polynucleotide (2), (4), (6), (8), (10) or (12), and inhibiting the biosynthesis of the polypeptide (1), (3), (5), (7), (9) or (11).

The invention also relates to polynucleotide (14) having all or part of the sequence of the antisense strand of the polynucleotide (2), (4), (6), (8), (10) or (12) that has undergone spontaneous or induced mutation, and inhibiting the biosynthesis of the polypeptide (1), (3), (5), (7), (9) or (11).

The invention also relates to polypeptide (15) containing in the molecule at least an amino acid sequence described as SEQ ID NO: 11 in the Sequence Listing.

The invention also relates to polynucleotide (16) containing in the molecule at least a base sequence described as SEQ ID NO: 10 in the Sequence Listing.

The invention also relates to polypeptide (17) containing in the molecule at least an amino acid sequence described as SEQ ID NO: 17 in the Sequence Listing.

The invention also relates to polynucleotide (18) containing in the molecule at least a base sequence described as SEQ ID NO: 16 in the Sequence Listing.

The invention also relates to polypeptide (19) containing in the molecule at least an amino acid sequence described as SEQ ID NO: 13 in the Sequence Listing.

The invention also relates to polynucleotide (20) containing in the molecule at least a base sequence described as SEQ ID NO: 12 in the Sequence Listing.

The invention also relates to polypeptide (21) containing in the molecule at least an amino acid sequence described as SEQ ID NO: 15 in the Sequence Listing.

The invention also relates to polynucleotide (22) containing in the molecule at least a base sequence described as SEQ ID NO: 14 in the Sequence Listing.

The invention also relates to polypeptide (23) containing in the molecule at least the polypeptide of (19) or (21).

The invention also relates to polynucleotide (24) containing in the molecule at least the polynucleotide of (20) or (22).

The invention also relates to polypeptide (25) containing the amino acid sequence of the polypeptide (15), (17), (19), (21) or (23) that has undergone spontaneous or induced mutation, and having the ability to bind a polypeptide containing a phosphorylated tyrosine residue.

The invention also relates to polynucleotide (26) encoding the polypeptide (25).

The invention also relates to polynucleotide (27) having all or part of the sequence of the antisense strand of the polynucleotide (14), (18), (20), (22), (24) or (26), and inhibiting the biosynthesis of the polypeptide (15), (17), (19), (21), (23) or (25).

The invention also relates to polynucleotide (28) having all or part of the sequence of the antisense strand of the polynucleotide (16), (18), (20), (22), (24) or (26) that has undergone spontaneous or induced mutation, and inhibiting the biosynthesis of the polypeptide (15), (17), (19), (21), (23) or (25).

The invention also relates to a recombinant plasmid containing the polynucleotide (2), (4), (6), (8), (10), (12), (14), (18), (20), (22), (24) or (26).

The invention also relates to recombinant microorganism cells transformed with the above plasmid.

The invention also relates to an antibody to a polypeptide having the amino acid sequence of (1), (3), (5), (7), (15), (17), (19) or (21).

The invention also provides a method of separating a polypeptide having the amino acid sequence of (1), (3), (5), (7), (15), (17), (19) or (21) by use of the above antibody.

The invention also provides a method of measuring tyrosine kinase activity in a cell or tissue, which comprises separating polypeptide having the amino acid sequence of (1), (3), (5), (7), (15), (17), (19) or (21) by use of the above antibody, and detecting a phosphorylated tyrosine residue in the separated polypeptide.

Embodiments of the present invention will be described in detail below.

For the identification and isolation of a novel brain-specific adapter molecule concerned with the invention, cells derived from any regions of the brain may be used. They may be cells from the hippocampus or caudate nucleus. Cells from the human or rat cerebrum are used preferably.

To identify the novel brain-specific adapter molecule, various chemical structural properties or biological chemical properties that the novel brain-specific adapter molecule requires to function as a phosphorylated signaling control factor may be utilized, and used as markers for search. For this purpose, it is possible to utilize the properties that the novel brain-specific adapter molecule binds to phosphorylated tyrosine on a specific polypeptide (say, NGF receptor) known to act as a signal molecule in a signal transmission system from a cell membrane or within a cell. In the present invention, structural similarity to the chemical structure of, say, Shc molecule, known to act as an adapter molecule in the NGF signaling system may be used as a search marker for the novel brain-specific adapter molecule. With the Shc, there have been known some partial peptide structures that may be essential for activity as the adapter molecule of the NGF signaling system. The relations of these structures with the respective activities are also under investigation. Such structures include the PTB (phosphorylated tyrosine binding) domain, the Gbr2 binding site, and the SH2 domain. Thus, whether an amino acid sequence highly homologous to the amino acid sequence of any of these specific regions is included or not can be used as an evaluation criterion. As this method of evaluation, there can be used, although not limited to, various methods based on comparisons with known Shc amino acid sequences (for instance, evaluation of a significant difference by calculation of homology to these amino acid sequences).

The form of samples for search is not limited in the present invention. Methods are usable which enable polypeptides having the above-described properties to be identified and isolated from cells directly or indirectly in a suitable manner (e.g., screening of an expression library using antibodies to Shc or its partial peptide). Alternatively, a method of searching for and identifying a gene encoding the polypeptide from a suitable cDNA library (for instance, random sampling) can be used. In the present invention, it is particularly preferred that a group of cDNA's selected from a suitable cDNA library by random sampling is used as samples for search.

(Preparation of cDNA Library)

For the selection of the above-mentioned suitable cDNA library, the present invention involves no limitations, and cDNA libraries available from various marketed products can be used. In the present invention, normalized cDNA library can be used particularly preferably. This is obtained, for example, by the method of Sasaki et al. (DNA Research 1, 91–96, 1994), and contains the uniform amounts of the respective cDNA's.

(Cloning of FC99 Gene cDNA)

In the present invention, there is no restriction on the extent of screening of the resulting normalized human brain cDNA library. Part of this library can be selected by a suitable sampling method. In this invention, screening of about $1 \times 10^3$ to $5 \times 10^3$ clones is preferred.

The way of obtaining a plasmid during screening is not restricted, and may be an ordinary known method. An example of this method is to cut out the insert by digestion with a restriction enzyme, and incorporate it into a plasmid vector using a ligase (e.g., Cell Engineering Experiments Protocol, by Yamamoto et al., Shujunsha, 71–107, 1991); or is in vivo excision using a helper phage (e.g., the method described in Uni-ZAP XR Cloning Kit Instruction Manual, by Stratagene). In the invention, conversion into the form of a plasmid by in vivo excision using a helper phage is particularly preferred.

(Determination of Base Sequence)

By determining the base sequence of the insert of the so obtained plasmid, it becomes possible to select a plasmid containing a gene encoding an amino acid sequence highly complementary to the aforementioned two characteristic domains of the Shc. The invention imposes no restriction on whether to analyze part or whole of the insert. Preferably, it is also possible in the invention to determine a base sequence of a suitable length and select a more suitable plasmid based on the results. That is, it is preferred in the invention to determine several base sequences at the 5'-terminal, predict amino acid sequences encoded by the determined base sequences, and select a plasmid on the basis of the results. In this case, at least 200 bases are preferably analyzed for the insert at the 5'-terminal. This is necessary to evaluate homology to the aforesaid domains.

The way of determining the base sequence at the 5'-terminal of the selected plasmid (not restricted; for example, can be selected randomly in a suitable number) is not restricted in the invention, but may be a known method. For instance, a method relying on Taq cycle sequencing (Biotechniques, 7, 494–499, 1989) is usable particularly preferably.

The method of comparison with the known Shc on the basis of the amino acid sequence from the resulting base sequence is not restricted, but homology analysis by an ordinary method can be performed. For example, homology analysis becomes possible by use of a commercially available program (e.g., GENETYX program (Ver. 27, Software Development Co.)) and protein database (e.g., protein database (NBRF, Release 43)). This homology analysis permits the selection of, say, a sequence with 30% or higher homology in consecutive 100 residues to the sequence of the Shc.

For more detailed analysis of the plasmid selected in the above manner, screening is done for isolating a clone containing the whole of the region encoding the protein of interest. No restriction is imposed on the way of the screening. In the invention, the 5'-terminal base sequence information obtained above is used preferably. There is no restriction on whether all or some of the base sequences should be used. It is enough that screening can be carried out using these base sequences. For instance, about a half of the resulting base sequences may be utilized. This is dependent on the screening method to be used.

Various known methods can be used preferably, and without restriction, for screening. For example, hybridization using a labeled oligonucleotide, or RACE using a primer heading in the 5'-direction or 3'-direction is particularly preferred. In the invention, screening is preferably performed by hybridization using as a probe a labeled oligonucleotide having a PTB domain-encoding base sequence among the base sequences obtained above. There is no restriction on the labeling, $[\alpha\text{-}^{32}P]$dCPT or digoxigenin can be used preferably. The conditions for hybridization are not restricted, and various known conditions are usable preferably (e.g., Cell Engineering Experiments Protocol, by Yamamoto et al., Shujunsha, 57–65, 1991).

The method of determining the base sequence of the insert from the positive clone screened in the above manner is not restricted, but various known methods can be used. An example is to produce deletion mutants, determine the base sequences of the respective clones, and join them together.

The above-described various known methods can be used to determine the base sequence of the longest insert of the inserts obtained above. An example is to prepare sequence primers successively from the portion having the base sequence determined, and read them.

(Determined FC99 Base Sequence)

A polynucleotide containing a base sequence encoding the determined human FC99 polypeptide is represented by SEQ ID NO: 2 in the Sequence Listing or SEQ ID NO: 8 in the Sequence Listing.

This polynucleotide related to the present invention includes a polynucleotide comprising a base sequence having no ATG linked to the 5'-terminal of SEQ ID NO: 2 in the Sequence Listing or SEQ ID NO: 8 in the Sequence Listing.

The polynucleotide of the invention also includes DNA containing 5'-flanking polynucleotide.

Also, part pf the structure of polynucleotide and the structure of a polypeptide deduced therefrom can be mutated spontaneously or artificially without changing the main activity (phosphorylated tyrosine binding capacity).

Thus, the polynucleotide of the invention also contains a base sequence encoding a polypeptide having a structure corresponding to a homologous isomer of the polypeptide of the invention.

Furthermore, at least one base of the base sequence of a polynucleotide can be replaced by another kind of base, without changing the amino acid sequence of a polypeptide produced from the polynucleotide, in accordance with the degeneracy of the genetic code. Thus, the polynucleotide of the invention can also contain a base sequence converted by substitution based on the degeneracy of the genetic code. For example, an amino acid sequence deduced from a base sequence obtained by such substitution performed for the base sequence of SEQ ID NO: 2 in the Sequence Listing or SEQ ID NO: 8 in the Sequence Listing agrees with the amino acid sequence of SEQ ID NO: 1 in the Sequence Listing or SEQ ID NO: 7 in the Sequence Listing, respectively.

(Amino Acid Sequence of FC99)

The amino acid sequence of FC99 is estimated from the polynucleotide determined by the foregoing method. The amino acid sequence of the FC99 polypeptide is described as SEQ ID NO: 1 or 7 in the Sequence Listing.

The amino acid sequence relevant to the invention also includes a polypeptide having no methionine joined to the N-terminus of the amino acid sequence.

Also, part of the structure of the polynucleotide encoding a polypeptide can be varied by spontaneous or artificial mutation (e.g., Molecular Cloning, A Laboratory manual, 2nd ed., Cold Spring Harbor Laboratory Press, 15.1–15.113, 1989) without changing the main activity of the polypeptide. The polypeptide of FC99 related to the invention also includes a polypeptide having a structure corresponding to a homologous mutant of the polypeptide having the above-mentioned amino acid sequence.

(Characteristics as Adapter Molecule)

The amino acid sequence translated from the determined base sequence shows significant homology to the known human Shc as depicted in FIG. 1. Actually, the base sequence, and the amino acid sequence based thereon, of the PTB domains shown in SEQ ID NO: 4 of the Sequence Listing and SEQ ID NO: 3 of the Sequence Listing bear homology of 77.4% to human Shc (see FIG. 1 upper side A).

Homology to human Shc in the SH2 domain shown in SEQ ID NO: 6 and SEQ ID NO: 5 of the Sequence Listing is found to reach 67.7% (see FIG. 1 bottom side B).

Comparison of FC99 obtained in the invention with Shc has shown that the FC99 retains tyrosine residues which undergo phosphorylation (Shc has been shown to bind to Grb2, another adapter molecule, via this phosphorylated tyrosine (van der Geer et al., Current Biology, 5, 404–412, 1995)) indispensable for Shc to act as an adapter molecule in intracellular signaling pathways.

(FC99-containing Transformed *E. coli*)

A suitable strain of *Escherichia coli* (*E. coli*) can be transformed with a clone containing the longest insert obtained above (e.g., Cell Engineering Experiments Protocol (Shujunsha, 1991), 105–107).

*E. coli* transformed in the above-described fashion with pBluescriptSK−, plasmid containing a polynucleotide having the base sequence described as Seq. ID No. 8 in the Sequence Listing was named pBS-FC99, and deposited on Oct. 11, 1995 at the National Institute of Bioscience and Human Technology (1–3, Higashi 1-chome, Tsukuba-shi, Ibaraki-ken 305 JAPAN), Agency of Industrial Science and Technology, Ministry of International Trade and Industry (accession number: FERM P-15228). This transformant was transferred to international deposition on Sep. 25, 1996 (accession number: FERM BP-5671).

(Preparation of Anti-FC99 Antibody and Detection of FC99 Protein)

Antibodies can be prepared in accordance with the method described in "Antibodies: A Laboratory Manual" (Cold Spring Harbor Laboratory Press, 1988) using a part or whole of one of polypeptides consisiting of the amino acids described as Seq. ID Nos. 1, 7, 3, 5, 11, 17, 13 and 15 in the Sequence Listing, or using purified FC99 protein. The polypeptide used is desirably one having antigenicity and more than 8 amino acid residues long. To obtain antisera by immunizing the rabbit with the polypeptide, for instance, can be easily practiced by known means. If polyclonal antibody with adequate antibody titer is obtained by immunization as the results of Example 3 show, monoclonal antibody can be easily produced by a hybridoma with lymphocytes of an immunized animal (e.g., "Antibodies: A Laboratory Manual" (Cold Spring Harbor Laboratory Press, 1988)). Thus, production of monoclonal antibody in the invention is easy for those skilled in the art.

Using the so obtained antibody, FC99 can be identified and detected by western blotting. That is, a sample containing FC99 protein is flowed over polyacrylamide gel, and reacted with the above-described antibody, whereby a band corresponding to the FC99 protein can be detected. This method can be performed following a known method as described in "Antibodies: A Laboratory Manual" (Cold Spring Harbor Laboratory Press, 1988).

(Detection of Activated Tyrosine Kinase Using Anti-FC99 Antibody)

The Shc protein is known to be a good substrate for a wide variety of tyrosine kinases. According to Oncogene (1995), 11, pp. 899–907, for example, a high degree of phosphorylation of Shc is detected in almost all types of cancer where activation of tyrosine kinase takes part (about a two-digit difference from normal tissues is observed). Such types of cancer include types where a tyrosine kinase receptor such as EGF receptor is involved, and types where a cytoplasmic tyrosine kinase such as src is involved. Thus, tyrosine kinases are estimated to play some role in about a half of all types of cancer. Against those types of cancer which the activation of tyrosine kinase takes part in, an inhibitor of tyrosine kinase must be effective as an anti-cancer drug. Thus, the validity of this chemotherapy may be evaluated by measuring high phosphorylation of Shc.

This discussion may hold true of the FC99 protein which belongs to the same family as the Shc protein. In other words, it may be possible to separate the FC99 protein by use of anti-FC99 antibody, and detect the phosphorylation of the tyrosine residue of the separated FC99 protein. Actually, as described in detail in Example 5, immunoprecipitation is performed using an antibody which recognizes the FC99 protein, whereafter the precipitate is reacted with anti-phosphorylated tyrosine antibody. This experiment shows that the tyrosine residue of the FC99 protein is phosphorylated with activated EGF receptor. Thus, the FC99 protein is separated by immunoprecipitation using an FC99 protein-recognizing antibody or an equivalent method, and then the degree of phosphorylation of its tyrosine residue is investigated. This may be able to provide a method of screening for the presence of activated tyrosine kinase in a cell or tissue. Hence, as with the previous discussion on Shc, this method will open up a use of assessing the validity of chemotherapy for cancer.

(Isolation of Rat FC99 Gene, and Its Base Sequence and Amino Acid Sequence)

The ways of isolating rat-derived FC99 gene, determining the base sequence of the resulting gene, and determining an amino acid sequence on the basis of the results are substantially the same as those explained in detail in regard to the human FC99 gene. More details will be offered in Example 6 to follow.

As with the human FC99 gene, a polynucleotide having the whole or part of the determined base sequence encoding the rat FC99 polypeptide is represented by SEQ ID NO: 10 and 16 in the Sequence Listing.

(Amino Acid Sequence of Rat-derived FC99)

The amino acid sequence of the polypeptide of rat-derived FC99, estimated from the polynucleotide encoding the polypeptide of rat-derived FC99 whose base sequence has been determined in the foregoing manner, is represented by SEQ ID NO: 11 and 17 in the Sequence Listing.

The rat FC99, like the human FC99, is found to show significant homology to the known Shc. That is, the polynucleotides of the PTB and SH2 domains are indicated as SEQ ID NO: 12 and 14, respectively, in the Sequence Listing. The polypeptides of the PTB and SH2 domains based on them are indicated as SEQ ID NO: 13 and 15, respectively, in the Sequence Listing.

The amino acid sequence translated from the determined base sequence shows significant homology to the known mouse Shc. Homologies for the amino acid sequences of the PTB and SH2 domains are 72.6% and 70.8%, respectively.

(Rat FC99-containing Transformed E. coli)

A suitable strain of E. coli can be transformed with a clone containing the longest insert obtained above (see, for example, Cell Engineering Experiments Protocol (Shujunsha, 1991), 105–107).

E. coli transformed in the above-described fashion with pBluescriptSK⁻, plasmid containing a polynucleotide having the base sequence described as SEQ ID NO: 16 in the Sequence Listing, was named pBS-R99, and deposited on Feb. 1, 1996 at the National Institute of Bioscience and Human Technology (1–3, Higashi 1-chome, Tsukuba-shi, Ibaraki-ken 305 JAPAN), Agency of Industrial Science and Technology, Ministry of International Trade and Industry (accession number: FERM P-15419). This transformant was transferred to international deposition on Sep. 25, 1996 (accession number: FERM BP-5672).

In the instant specification, the following abbreviations will be used, if desired.
DNA Deoxyribonucleic acid
A Adenine
C Cytosine
G Guanine
T Thymine
Ala (A) Alanine
Arg (R) Arginine
Asn (N) Asparagine
Asp (D) Aspartic acid
Cys (C) Cysteine
Gln (Q) Glutamine
Glu (E) Glutamic acid
Gly (G) Glycine
His (H) Histidine
Ile (I) Isoleucine
Leu (L) Leucine
Lys (K) Lysine
Met (M) Methionine
Phe (F) Phenylalanine
Pro (P) Proline
Ser (S) Serine
Thr (T) Threonine
Trp (W) Tryptophan
Tyr (Y) Tyrosine
Val (V) Valine The present invention will be described in detail based on the following working examples. However, these examples are offered by way of illustration, and do not limit the invention.

EXAMPLES

Example 1

Construction of Human Brain-derived Uniformed cDNA Library

A normalized cDNA library was constructed using human cerebral mRNA. Normalization was performed by the method of Sasaki et al. (DNA Research 1, 91–96, 1994) involving the steps (i), (ii) and (iii): (i) self hybridization in a semi-solid phase system, (ii) preparation of a phage cDNA library from mRNA treated in (i), and (iii) conversion from insert cDNA into cRNA. These steps were performed in the sequence (i), (ii), (iii), (i), (ii) to construct the normalized cDNA library.

Human FC99 Gene cDNA Cloning (1) Of 1 ml of the uniformed cDNA library constructed in the above manner, 100 $\mu$l was converted into a plasmid in accordance with in vivo excision (the method described in Stratagene's Uni-ZAP XR Cloning Kit Instruction Manual) using a helper phage (EXAssist helper phage, Stratagene).

More specifically, 200 $\mu$l of E. coli XL-1Blue, 100 $\mu$l of the uniformed cDNA library, and 1 $\mu$l of helper phage R408 (>1×10⁶ pfu/ml) were mixed in a 50 ml test tube, and the E. coli was infected with ZAP and the helper phage for 15 minutes at 37° C.

5 ml of 2×YT culture medium (10 g NaCl, 10 g Bacto Yeast Extract, 16 g Bactotryptone/11) was added; and the mixture was shake cultured for 3 hours at 37° C., causing the E. coli to secrete phagemid.

After heat treatment for 20 minutes at 70° C., centrifugation was performed for 5 minutes at 4000 g to eradicate the cells. The supernatant phagemid was transferred into another test tube.

This supernatant contained pBluescriptSK(−) particles. 200 microliters of this supernatant, or 20 $\mu$l 1 of a 1:100 dilution of this supernatant was mixed with 200 μl of XL-1 Blue (OD600=1.0) for 15 minutes at 37° C. for infection.

The cultured medium (1 to 100 μl) was plated on LB/Amp plate, and cultured overnight at 37° C. The resulting colonies were *E. coli* (XL-1 Blue) transformants with double strand pBluescriptSK(−) containing the insert DNA.

(2) Plasmids were prepared from this *E. coli* by means of QIAwell 8 Plus kit (Qiagen).

(3) The sequences at the 5'-terminals of the inserts of the resulting plasmids were determined by Taq cycle sequencing (Biotechniques, 7, 494–499, 1989) using Perkin-Elmer's autosequencer 373A.

(4) The amino acid sequences obtained by translating the determined base sequences were compared with protein database (NBRF, Release 43) under the GENETYX program (Ver. 27, Software Development Co.) to analyze homology.

(5) The above-described sequence determination and homology analysis of more than 500 plasmids were performed. One plasmid containing the PTB domain and the SH2 domain was selected (designated as FC99; FC=forebrain cortex). For more detailed analysis, clones containing the whole of the region encoding the protein were isolated in the manner described below.

(6) Screening was performed using frontal cortex-derived cDNA library (Stratagene) and a part of the PTB domain of these clones (its base sequence is indicated as Seq. ID No. 9 in the Sequence Listing) as a probe.

A phage library solution (20 μl) and *E. coli* XL-1 Blue (200 μl) were cultured for 15 minutes at 37° C. The cultured medium was added to 2 to 3 ml of top agar (heated at 48° C.), and the mixture was plated on an NZY agar plate, and cultured overnight at 37° C.

About 50,000 plaques were cultured on each of six 100 mm square plates. These about $3 \times 10^5$ plaques were used for screening.

The NZY plate was cooled for 2 hours at 4° C., whereafter a nylon filter (HIGHBOND N+, Amersham) was placed on the plate, and allowed to stand for 2 minutes.

The nylon filter was peeled off, dried on a filter paper, and immobilized with UV rays to prepare a screening filter.

Hybridization was performed by the following procedure:

A probe for hybridization was a DNA fragment having the above-mentioned base sequence, the fragment being labeled with $^{32}$P-dCTP (Amersham) by means of a megaprime labeling kit (Amersham).

A prehybridization solution used contained 5×SSC (0.15M NaCl, 0.015M sodium citrate (pH 7.0)), 50% formamide, 1xdenhardt solution (0.2% bovine serum albumin (Fraction V), 0.2% polyvinyl pyrrolidone, 0.2% Ficoll400), 0.1% SDS, and 100 μg/ml salmon sperm DNA.

The filter was incubated in the prehybridization solution for 3 hours at 42° C., and incubated in a hybridization solution (the prehybridization solution containing 10% dextran sulfate) containing the labeled probe for 16 hours at 42° C. to perform hybridization.

Eight positive clones were obtained. The center of plaques of the positive ZAP phage clones in the resulting agar plates was dug out with a Pasteur pipette, and dissolved in a mixture of 500 μl SM buffer solution and 20 μl chloroform. The solution was vortex stirred, and then allowed to stand overnight.

200 μl of *E. coli* XL-1Blue, 200 μl of the positive phage clones (>1×10$^5$ phage particles), and 1 μl of helper phage R408 (>1×10$^6$ pfu/ml) were mixed in a 50 ml test tube, and the *E. coli* was infected with ZAP and the helper phage for 15 minutes at 37° C.

5 ml of 2×YT culture medium (10 g NaCl, 10 g Bacto Yeast Extract, 16 g Bactotryptone/11) was added, and the mixture was shake cultured for 3 hours at 37° C., causing the *E. coli* to secrete phagemid. The secretions were heat treated for 20 minutes at 70° C., and centrifuged for 5 minutes at 4000 g to eradicate the cells. The phagemid of the resulting supernatant was transferred into another test tube.

This supernatant contained pBluescript particles. 200 microliters of this supernatant, or 20 μl of a 1:100 dilution of this supernatant was mixed with 200 μl of XL-1 Blue (OD600=1.0) for 15 minutes at 37° C. for infection.

The cultured medium (1 to 100 μl) was plated on LB/Amp plates, and cultured overnight at 37° C. The resulting colonies were *E. coli* (XL-1 Blue) transformants with double stranded pBluescriptSK(−) containing the insert DNA.

Plasmids were prepared from the *E. coli* of the eight positive clones by means of a QIAprepPlasmid kit (Qiagen). For the clones with the longest insert (insert of about 2.5 kb), DNA base sequence determination was performed in the following manner:

(7) The base sequence of the 2.5 kb clone was determined by Taq cycle sequencing (Biotechniques, 7, 494–499, 1989) using Perkin-Elmer's autosequencer 373A. As a result, two sites were found feasible as the initiation point of translation. Of the analyzed base sequences of the cDNA's of FC99, 1425 bases starting at one of the initiation points of translation are indicated as SEQ ID NO: 2 in the Sequence Listing, while 1785 bases starting at the other initiation point of translation are indicated as SEQ ID NO: 8 in the Sequence Listing. The amino acid sequences encoded by the cDNA's are indicated as SEQ ID NOS: 1 and 7, respectively, in the Sequence Listing.

Analysis of FC99 Gene-encoded Amino Acid Sequences

The amino acid sequences translated from the determined base sequences contain two domains, PTB domain and SH2 domain, that are known to recognize phosphorylated tyrosine (its biochemical mechanisms are described, for example, in Heumann: Current opinion in Neurobiology, 4, 668–679, 1994, or Pawson: Nature, 373, 573–580, 1995), a known signal molecule in the signaling pathways in neurons of the brain (e.g., the signaling pathways in neurons where NGF acts) as shown in FIG. 2.

The structure of FC99 also closely resembles that of Shc, an adapter molecule in the intracellular signaling pathways, at the two sites, the PTB domain and the SH2 domain (see FIG. 1). Actually, homology for the PTB domain is 77.4%, and homology for the SH2 domain is 67.7%. Furthermore, tyrosine residues to be phosphorylated (Shc has been shown to bind Grb2, another adapter molecule, via this phosphorylated tyrosine), a tool indispensable for Shc to act as an adapter molecule in intracellular signaling pathways, are well retained between FC99 and Shc.

Example 2

Comparison of the Level of Expression of the FC99 Gene Among 16 Kinds of Cells

This comparison was made by northern blotting in accordance with the method described in Molecular Cloning, A Laboratory Manual, 2nd ed., Cold Spring Harbor Laboratory Press, 7.39–7.52, 1989. Human multiple tissue northern blots (Clontech) were produced by agarose electrophoresing polyA+RNA, extracted from 2 μg each of the heart, brain, placenta, lung, liver, skeletal muscle, kidney and pancreas, and then transferring the electrophoresed products onto a membrane. Human multiple tissue northern blots II (Clontech) were produced by agarose electrophoresing polyA+RNA, extracted from 2 μg each of the spleen, thymus, testicle, prostate, ovary, small intestine, large intestine, and peripheral lymphocytes, and then transferring the electrophoresed products onto a membrane.

A probe for hybridization was a DNA fragment having the base sequence described as SEQ ID NO: 9 in the Sequence Listing, the fragment being labeled with 32P-dCTP (Amersham) by means of a megaprime labeling kit (Amersham).

A prehybridization solution used contained 50% formamide, 5×denhardt solution (1% bovine serum albumin (Fraction V), 1% polyvinyl pyrrolidone, 1% Ficoll400), 0.5% SDS, 5×SSC (0.15M NaCl, 0.015M sodium citrate (pH 7.0)), and 100 μg/ml salmon sperm DNA.

The filter was incubated in the prehybridization solution for 3 hours at 42° C., and incubated in a hybridization solution (a solution of the same composition as the prehybridization solution) containing the labeled probe for 16 hours at 42° C. to perform hybridization.

After washing, the membrane was placed for 2 days at −80° C. in intimate contact with an X-ray film, and then developed. The results of quantitative determination of the densities of the respective bands on the X-ray film by means of a densitometer are shown in FIG. 2.

Example 3
Production of Anti-FC99 Antibody

The production of the antibody was performed in the following manner in accordance with the method described in Chapter 5 of "Antibodies: A Laboratory Manual" (Cold Spring Harbor Laboratory Press, 1988):

Two peptides included in both of the amino acid sequences described as SEQ ID NOS: 1 and 7 in the Sequence Listing, (I) PWTEEEGDGSDHPYYN (the sequence as SEQ ID NO: 18 in the Sequence Listing) and (II) QTPLRQGSSDIYSTP (the sequence as SEQ ID NO: 19 in the Sequence Listing), were each synthesized in the form of having cysteine added to the C-terminus, and conjugated to a carrier protein, KLH (Keyhole Limpet Hemocyanin), by the MCS (heterocrosslinking reagent) method. Then, the rabbit was immunized twice with the conjugation product at an interval of 2 weeks. Blood samples were taken 5 and 6 weeks after the initial immunization, and measured for the antibody titer by the ELISA method using the peptide used in the immunization. With each of the peptides I and II, the antibody titer increased more than 16,000-fold at 6 weeks. At this time, antiserum (antibody) was collected in a large amount, and a part of the antiserum was used in experiments of Example 4.

Example 4
Detection of FC99 Protein by Anti-FC99 Antibody

Figure 3:
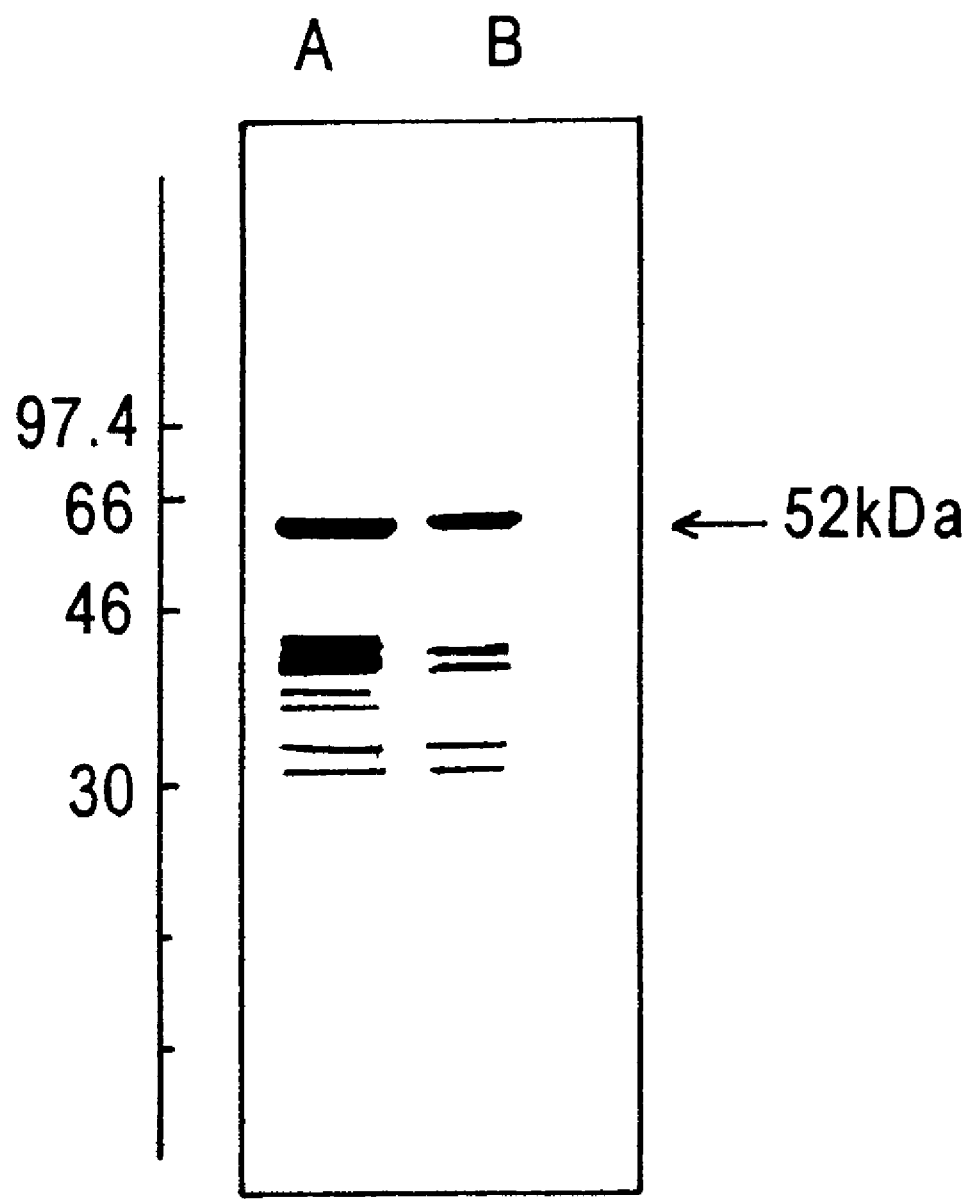
FIG. 3 is a photograph showing the results of detection of FC99 protein by western blotting using anti-FC99 antibody, FIG. 3 lane A and lane B corresponding to peptides I and II, respectively, of Example 3, both having a band at 52 kDa (indicated by the arrow)

A base sequence encoding the amino acid sequence described as SEQ ID NO: 1 in the Sequence Listing was inserted between the HindIII site and the XbaI site of the pRc/CMV plasmid (Invitrogen). The plasmid was introduced into COS-1 cells using LipofectAmine (Gibco-BRL) (the introduction followed the manual attached to the LipofectAmine). After 48 hours of culture, a cell extract was prepared (this cell extract would contain a polypeptide corresponding to the amino acid sequence described as SEQ ID NO: 1 in the Sequence Listing). The cell extract was electrophored on a polyacrylamide gel, and analyzed by western blotting using the two kinds of antibodies prepared in Example 3. In both cases, bands corresponding to the FC99 protein having the amino acid sequence described as SEQ ID NO: 1 were detected at the position of 52 kDa (the bands by the antibodies based on the peptides I and II of Example 3 are shown in FIG. 3 parts A and, the band for 52 kDa being shown by the arrow in the drawing). The analyses by western blotting followed the method described in Chapter 12 of "Antibodies: A Laboratory Manual" (Cold Spring Harbor Laboratory Press, 1988).

Example 5
Involvement of FC99 Protein in Signal Transmission of Epidermal Growth Factor (1) A base sequence was prepared by adding a base sequence, which encodes T7 peptide (Met-Ala-Ser-Met-Thr-Gly-Gly-Gln-Gln-Met-Gly) (the sequence as SEQ ID NO: 20 in the Sequence Listing), to the 5'-terminus of a base sequence encoding the amino acid sequence described as SEQ ID NO: 1 in the Sequence Listing. The resulting base sequence was inserted between the HindIII site and the Xba I site of the pRc/CMV plasmid (Invitrogen).

(2) For use in immunoprecipitation, anti-T7 peptide antibody (Novagen) was covalently bonded to protein A-Sepharose (Pharmacia) in accordance with the method described on pages 521 to 523 of "Antibodies Laboratory Manual".

(3) The plasmid prepared in (1) was introduced into COS-1 cells by use of LipofectAmine (Gibco-BRL) in accordance with a manual attached to the LipofectAmine to express T7 peptide-added FC99 protein having T7 peptide added to the N-terminal of the amino acid sequence described as SEQ ID NO: 1 in the Sequence Listing. After 18 hours of culture under low serum content conditions, EGF was administered to a concentration of 100 ng/ml (for control, no EGF was administered). Five minutes after EGF administration, a cell extract was prepared. The extract was immunoprecipitated using the anti-T7 peptide antibody covalently bonded to the protein A-Sepharose prepared in (2). This procedure was performed in accordance with an example described in Oncogene (1995), 11, 899–907.

Figure 4:
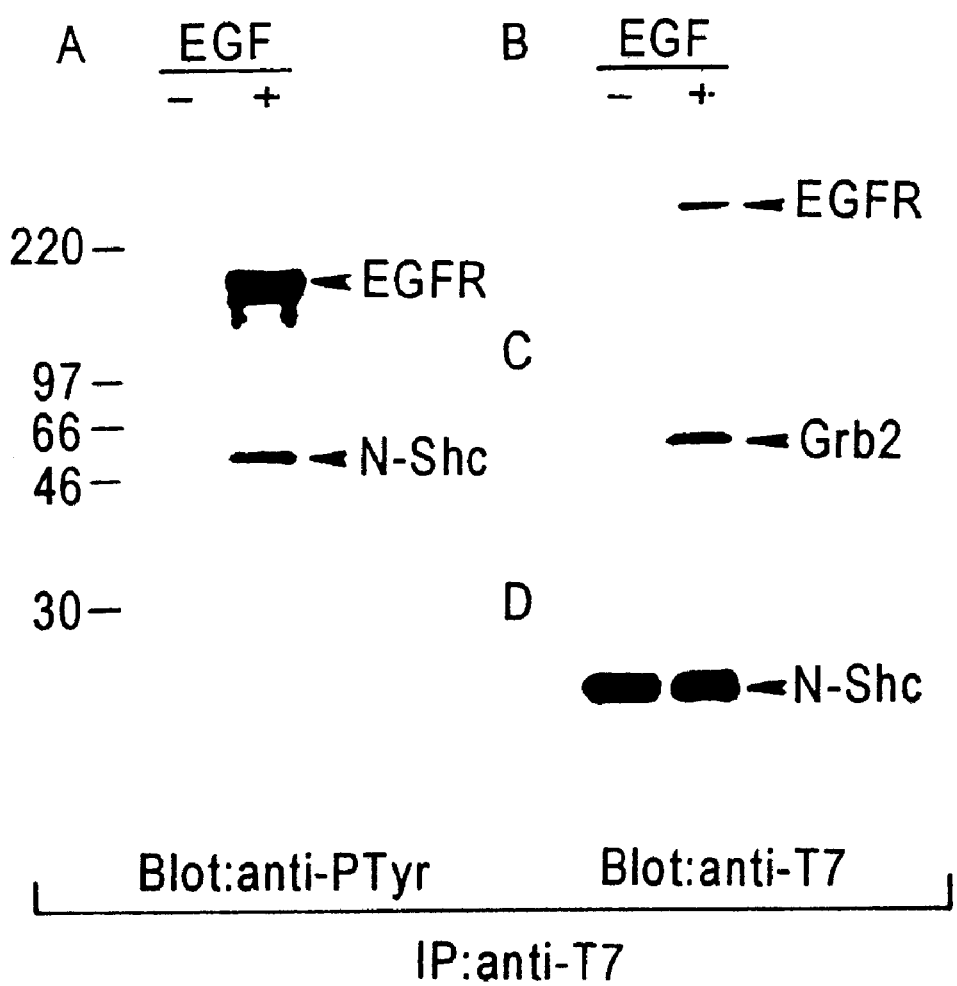
FIG. 4 is a photograph showing the results of detection of the effect of EGF on T7 peptide-added FC99 protein, expressed in COS-1 cells, by western blotting using part (A) anti-phosphorylated tyrosine antibody, part (B) anti-EGF receptor antibody, part (C) anti-Grb2 antibody, and part (D) anti-T7 peptide antibody. The numerals on the left denote molecular weights in kDa.

(4) The immunoprecipitate was electrophoresed on a polyacrylamide gel, and then analyzed by western blotting using (A) anti-phosphorylated tyrosine antibody, (B) anti-EGF receptor antibody, (C) anti-Grb2 antibody, and (D) anti-T7 peptide antibody. The results are shown in FIG. 4, parts B to D show only bands close to the colored regions. As shown in FIG. 4 part A, tyrosine phosphorylation of FC99 (N-Shc) occurred only when stimulated with EGF. On this occasion, another phosphorylated band appeared near 180 KDa. This band was found to be EGF receptor as shown in FIG. 4 part B. FIG. 4 part C also showed that FC99 and the adapter molecule Grb2 were joined together depending on stimulation with EGF. As seen in FIG. 4 part D, the amount of the immunoprecipitated T7 peptide-added FC99 protein did not change with the presence or absence of EGF. These findings demonstrated that EGF receptor activated by the administration of EGF bound FC99 to tyrosine phosphorylate the FC99, inducing the joining of the FC99 and the Grb2. Based on this fact, Grb2/SOS complex migrates close to the cell membrane, arousing the activation of ras by SOS.

Example 6
Cloning of Rat FC99 Gene cDNA (1) Screening was performed in the same manner as in Example 1(6) by using rat brain-derived cDNA library (Stratagene) and a part of the base sequence of human FC99 gene (the base sequence is indicated as Seq. ID No. 9 in the Sequence Listing) as a probe.

Plasmids were prepared from the *E. coli* of the five positive clones of the resulting *E. coli* (XL-1 Blue) transformants by means of a QIAprepPlasmid kit (Qiagen). For the clones with the longest insert (insert of about 4.1 kb), DNA base sequence determination was performed in the following manner:

(2) The base sequence of the resulting 4.1 kb clone was determined by Taq cycle sequencing (Biotechniques, 7, 494–499, 1989) using Perkin-Elmer's DNA sequencer 373A. As a result, two sites were found feasible as the initiation point of translation. Of the analyzed base sequences of the cDNA's of rat FC99, 1425 bases starting at one of the initiation points of translation are indicated as SEQ ID NO: 10 in the Sequence Listing, while 1785 bases starting at the other initiation point of translation are indicated as SEQ ID NO: 16 in the Sequence Listing. The amino acid sequences encoded by the cDNA's are indicated as SEQ ID NOS: 11 and 17, respectively, in the Sequence Listing.

Example 7

Involvement of FC99 Protein in Signal Transmission of Brain-derived Neurotrophic Factor BDNF (1) A base sequence was prepared by adding a base sequence, which encodes T7 peptide, (Met-Ala-Ser-Met-Thr-Gly-Gly-Gln-Gln-Met-Gly) (SEQ ID NO: 20), to the 5'-terminus of a base sequence encoding the amino acid sequence described as SEQ ID NO: 1 in the Sequence Listing. The resulting base sequence was inserted between the Hind III site and the Xba I site of the pRc/CMV plasmid (Invitrogen).

(2) For use in immunoprecipitation, anti-T7 peptide antibody (Novagen) was covalently bonded to protein A-Sepharose (Pharmacia) in accordance with the method described on pages 521 to 523 of "Antibodies Laboratory Manual".

(3) Only the plasmid prepared in (1), or the plasmid prepared in (1) together with the same amount of an expression vector for BDNF receptor (TrkB receptor, or simply TrkB), was introduced into NIH3T3 cells by use of the LipofectAmine (Gibco-BRL) in accordance with a manual attached to the LipofectAmine to express T7 peptide-added FC99 protein receptor having T7 peptide added to the N-terminal of the amino acid sequence described as Seq. ID No. 1 in the Sequence Listing or TrkB. After 18 hours of culture under low serum content conditions, BDNF was administered to a concentration of 100 ng/ml (for control, no BDNF was administered). Five minutes after BDNF administration, a cell extract was prepared. The extract was immunoprecipitated using the anti-T7 peptide antibody covalently bonded to the protein A-Sepharose prepared in (2). This procedure was performed in accordance with an example described in Oncogene (1995), 11, 899–907.

Figure 5:
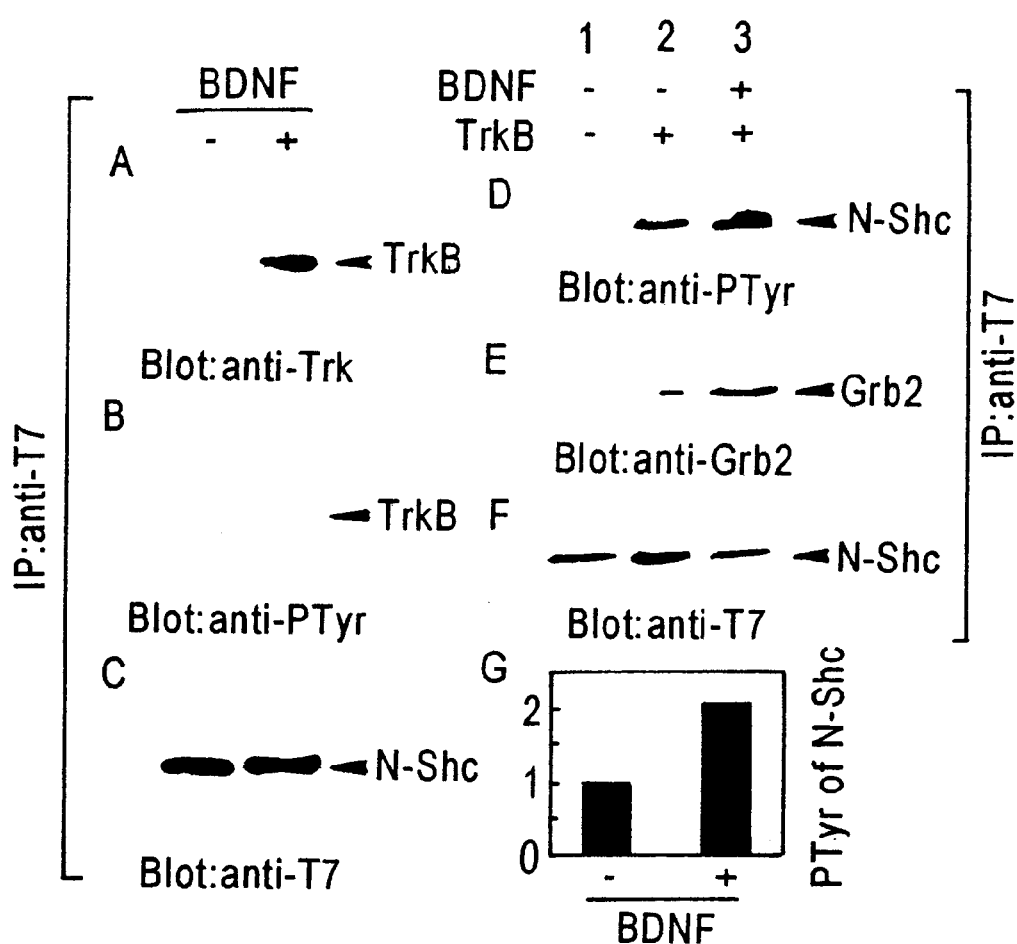
FIG. 5 is a photograph showing the results of detection of the effect of BDNF on the expression of T7 peptide-added FC99 protein in NIH3T3 cells by western blotting using part (A) anti-TrK receptor antibody, part (B) and part (D) anti-phosphorylated tyrosine antibody, part (C) and part (F) anti-T7 receptor antibody, and part (E) anti-Grb2 antibody; A to C being designed to study responses to BDNF in NIH3T3 cells incorporating both a plasmid expressing TrkB receptor and a plasmid expressing T7 peptide-added FC99 protein; parts D to F revealing the results of investigation in which the behaviors of T7 peptide-added FC99 protein in the presence and absence of BDNF and in the presence and absence of BDNF receptor (TrkB) were investigated by western blotting using part (D) anti-phosphorylated tyrosine antibody, part (E) anti-Grb2 antibody, and part (F) anti-T7 peptide antibody; and G showing the results of calibration on the photograph of part D by means of a scanner.

(4) The immunoprecipitate was electrophoresed on a polyacrylamide gel. Then, the immunoprecipitate from the cells incorporating both the plasmid prepared in (1) and the BDNF receptor expression vector was analyzed by western blotting using (A) anti-Trk receptor antibody, (B) anti-phosphorylated tyrosine antibody, and (C) anti-T7 peptide antibody. The results are shown in FIG. 5. As shown in FIG. 5 part A, TrkB was bound to FC99 only when stimulated with BDNF. Also, as shown in FIG. 5 part B, tyrosine phosphorylation of the TrkB receptor occurred upon stimulation with BDNF. As seen in FIG. 5 part C, the amount of the immunoprecipitated T7 peptide-added FC99 protein did not change with the presence or absence of BDNF. Likewise, analysis by western blotting was made using (D) anti-phosphorylated tyrosine antibody, (E) anti-Grb2 antibody, and (F) anti-T7 peptide antibody. The results are shown in FIG. 5 parts D to F. Lane 1 gives the results on the immunoprecipitate from the cells incorporating only the peptide prepared in (1) but not administered BDNF. Lane 2 offers the results on the immunoprecipitate from the cells incorporating the peptide prepared in (1) and TrkB, but not administered BDNF. A comparison between Lanes 2 and 3 in FIG. 5 parts D to F showed that tyrosine phosphorylation of the FC99 protein, and the binding of the FC99 protein and Grb2 increased depending on BDNF. The amount of the BDNF-dependent increase in the tyrosine phosphorylation of the FC99 protein was investigated by reading the photograph of FIG. 5 part D into a scanner (Model GT-6000, Epson), and comparing the densities of Lanes 2 and 3 by means of the NIH Image (an image analysis software of NIH, U.S.A.). The results, as in FIG. 5 part G, showed about 2-fold increase dependent on the administration of BDNF. A comparison of Lanes 1 and 2 in FIG. 5 parts D and E showed that the tyrosine phosphorylation of FC99 protein and the binding of FC99 protein and Grb2 in the absence of BDNF took place by the action of the TrkB receptor introduced together with the plasmid prepared in (1). These findings demonstrated that the TrkB receptor activated by the administration of BDNF formed a complex of the tyrosine-phosphorylated FC99 protein with Grb2. Based on this fact, the Grb2/SOS complex migrates close to the cell membrane, arousing the activation of ras by SOS.

Activation of ras by SOS is known to promote the growth of nerve cells (Rozakis-Adcock et al., Nature 360, 689–692, 1992). Thus, the polypeptides and polynucleotides of the present invention are expected to be useful for the diagnosis and treatment of diseases in which nerve cells are involved.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Application Nos. 265988/1995 filed on Oct. 13, 1995, 323069/1995 filed on Dec. 12, 1995, 069265/1996 filed on Feb. 29, 1996, and 212973/1996 filed on Jul. 24, 1996 are hereby incorporated by reference.

SEQUENCE LISTING

<160> NUMBER OF SEQ ID NOS: 24

<210> SEQ ID NO 1
<211> LENGTH: 474
<212> TYPE: PRT
<213> ORGANISM: Homo sapiens

<400> SEQUENCE: 1

Met Ser Ala Ala Arg Lys Gly Arg Pro Gly Asp Glu Pro Leu Pro Arg
 1               5                  10                  15

Pro Pro Arg Gly Thr Pro His Ala Ser Asp Gln Val Leu Gly Pro Gly
                20                  25                  30

Val Thr Tyr Val Val Lys Tyr Leu Gly Cys Ile Glu Val Leu Arg Ser
            35                  40                  45

Met Arg Ser Leu Asp Phe Ser Thr Arg Thr Gln Ile Thr Arg Glu Ala
        50                  55                  60

Ile Ser Arg Val Cys Glu Ala Val Pro Gly Ala Lys Gly Ala Phe Lys
 65                  70                  75                  80

Lys Arg Lys Pro Pro Ser Lys Met Leu Ser Ile Leu Gly Lys Ser
                85                  90                  95

Asn Leu Gln Phe Ala Gly Met Ser Ile Ser Leu Thr Ile Ser Thr Ala
                100                 105                 110

Ser Leu Asn Leu Arg Thr Pro Asp Ser Lys Gln Ile Ile Ala Asn His
            115                 120                 125

His Met Arg Ser Ile Ser Phe Ala Ser Gly Gly Asp Pro Asp Thr Thr
        130                 135                 140

Asp Tyr Val Ala Tyr Val Ala Lys Asp Pro Val Asn Arg Arg Ala Cys
145                 150                 155                 160

His Ile Leu Glu Cys Cys Asp Gly Leu Ala Gln Asp Val Ile Gly Ser
                165                 170                 175

Ile Gly Gln Ala Phe Glu Leu Arg Phe Lys Gln Tyr Leu Gln Cys Pro
            180                 185                 190

Thr Lys Ile Pro Ala Leu His Asp Arg Met Gln Ser Leu Asp Glu Pro
        195                 200                 205

Trp Thr Glu Glu Gly Asp Gly Ser Asp His Pro Tyr Tyr Asn Ser
        210                 215                 220

Ile Pro Ser Lys Met Pro Pro Gly Gly Phe Leu Asp Thr Arg Leu
225                 230                 235                 240

Lys Pro Arg Pro His Ala Pro Asp Thr Ala Gln Phe Ala Gly Lys Glu
                245                 250                 255

Gln Thr Tyr Tyr Gln Gly Arg His Leu Gly Asp Thr Phe Gly Glu Asp
            260                 265                 270

Trp Gln Gln Thr Pro Leu Arg Gln Gly Ser Ser Asp Ile Tyr Ser Thr
        275                 280                 285

Pro Glu Gly Lys Leu His Val Ala Pro Thr Gly Glu Ala Pro Thr Tyr
    290                 295                 300

Val Asn Thr Gln Gln Ile Pro Pro Gln Ala Trp Pro Ala Ala Val Ser
305                 310                 315                 320

Ser Ala Glu Ser Ser Pro Arg Lys Asp Leu Phe Asp Met Lys Pro Phe
                325                 330                 335

Glu Asp Ala Leu Lys Asn Gln Pro Leu Gly Pro Val Leu Ser Lys Ala
            340                 345                 350

Ala Ser Val Glu Cys Ile Ser Pro Val Ser Pro Arg Ala Pro Asp Ala
        355                 360                 365

Lys Met Leu Glu Glu Leu Gln Ala Glu Thr Trp Tyr Gln Gly Glu Met
    370                 375                 380

Ser Arg Lys Glu Ala Glu Gly Leu Leu Glu Lys Asp Gly Asp Phe Leu
385                 390                 395                 400

Val Arg Lys Ser Thr Thr Asn Pro Gly Ser Phe Val Leu Thr Gly Met

His Asn Gly Gln Ala Lys His Leu Leu Leu Val Asp Pro Glu Gly Thr
        405                 410                 415
                        420                 425                 430

Ile Arg Thr Lys Asp Arg Val Phe Asp Ser Ile Ser His Leu Ile Asn
                435                 440                 445

His His Leu Glu Ser Ser Leu Pro Ile Val Ser Ala Gly Ser Glu Leu
    450                 455                 460

Cys Leu Gln Gln Pro Val Glu Arg Lys Gln
465                 470

<210> SEQ ID NO 2
<211> LENGTH: 1425
<212> TYPE: DNA
<213> ORGANISM: Homo sapiens

<400> SEQUENCE: 2

| | | | | | |
|---|---|---|---|---|---|
| atgagcgccg | ccaggaaggg | ccggcccggc | gacgagccgc | tgcccaggcc | ccctcggggg | 60 |
| acgccgcacg | ccagcgacca | ggtgctgggg | cccggagtca | cctacgtggt | caagtacttg | 120 |
| gggtgcattg | aagttctgcg | ctcaatgagg | tctcttgact | tcagtacaag | aacacaaatt | 180 |
| accagggaag | ccatcagccg | cgtctgtgaa | gctgtgcctg | gtgcgaaggg | agccttcaag | 240 |
| aagagaaagc | ctccaagcaa | aatgctgtcc | agcatcttgg | gaaagagcaa | cctccagttt | 300 |
| gcgggaatga | gcatctctct | gaccatctcc | acggccagtc | tgaacctgcg | aactccggac | 360 |
| tccaaacaga | tcatagcgaa | tcaccacatg | cggtccatct | ccttcgcctc | tgggggagac | 420 |
| ccggacacaa | ctgactatgt | tgcatatgtg | gctaaggacc | ctgttaatcg | cagagcttgt | 480 |
| cacattttgg | aatgctgtga | tgggctggcc | caggatgtca | tcggctccat | cggacaagcc | 540 |
| tttgagctcc | ggtttaagca | atatttacag | tgtcctacca | agattcccgc | tctccatgat | 600 |
| cgaatgcaga | gtctggatga | gccatggacg | gaagaggagg | gagatggctc | agaccaccca | 660 |
| tactacaaca | gcatcccaag | caagatgcct | cctccagggg | gctttcttga | tactagactg | 720 |
| aaacccagac | cccatgctcc | tgacacagcc | cagtttgcag | aaaagagcaa | gacttattac | 780 |
| cagggaagac | acttaggaga | cacttttggc | gaagactggc | agcaaacacc | tttaaggcaa | 840 |
| gggtcctcgg | acatctacag | cacgccagaa | gggaaactgc | acgtggcccc | cacgggagaa | 900 |
| gcacccacct | acgtcaacac | tcagcagatc | ccaccacagg | cctggccggc | tgcggtcagc | 960 |
| agtgctgaga | gcagcccgag | gaaagacctc | tttgacatga | aaccttttga | agatgctctc | 1020 |
| aagaaccagc | ccttggggcc | cgtgttaagc | aaggcagcct | ccgtggagtg | catcagccct | 1080 |
| gtgtcaccta | gagccccaga | tgccaagatg | ctggaggaac | tgcaagccga | gacttggtac | 1140 |
| caaggagaga | tgagcaggaa | ggaggcagag | gggctgctgg | agaaagacgg | agacttcctg | 1200 |
| gtcaggaaga | gcaccaccaa | cccgggctcc | tttgtcctca | cgggcatgca | caatggccag | 1260 |
| gccaagcacc | tgctgctcgt | ggacccagaa | ggcacgatcc | ggacaaagga | cagagtcttt | 1320 |
| gacagtatca | gccacctcat | caaccaccac | ctagaaagca | gcctgcccat | tgtctctgca | 1380 |
| gggagtgagc | tgtgtctcca | gcagccagtg | gagaggaagc | agtga | | 1425 |

<210> SEQ ID NO 3
<211> LENGTH: 164
<212> TYPE: PRT
<213> ORGANISM: Homo sapiens

<400> SEQUENCE: 3

Leu Gly Pro Gly Val Thr Tyr Val Val Lys Tyr Leu Gly Cys Ile Glu

```
                  1               5                  10                  15
             Val Leu Arg Ser Met Arg Ser Leu Asp Phe Ser Thr Arg Thr Gln Ile
                             20                  25                  30

Thr Arg Glu Ala Ile Ser Arg Val Cys Glu Ala Val Pro Gly Ala Lys
                     35                  40                  45

Gly Ala Phe Lys Lys Arg Lys Pro Pro Ser Lys Met Leu Ser Ser Ile
                 50                  55                  60

Leu Gly Lys Ser Asn Leu Gln Phe Ala Gly Met Ser Ile Ser Leu Thr
             65                  70                  75                  80

Ile Ser Thr Ala Ser Leu Asn Leu Arg Thr Pro Asp Ser Lys Gln Ile
                             85                  90                  95

Ile Ala Asn His His Met Arg Ser Ile Ser Phe Ala Ser Gly Gly Asp
                            100                 105                 110

Pro Asp Thr Thr Asp Tyr Val Ala Tyr Val Ala Lys Asp Pro Val Asn
                        115                 120                 125

Arg Arg Ala Cys His Ile Leu Glu Cys Cys Asp Gly Leu Ala Gln Asp
                    130                 135                 140

Val Ile Gly Ser Ile Gly Gln Ala Phe Glu Leu Arg Phe Lys Gln Tyr
             145                 150                 155                 160

Leu Gln Cys Pro
```

<210> SEQ ID NO 4
<211> LENGTH: 492
<212> TYPE: DNA
<213> ORGANISM: Homo sapiens

<400> SEQUENCE: 4

```
ctggggcccg gagtcaccta cgtggtcaag tacttggggt gcattgaagt tctgcgctca    60
atgaggtctc ttgacttcag tacaagaaca caaattacca gggaagccat cagccgcgtc   120
tgtgaagctg tgcctggtgc gaagggagcc ttcaagaaga gaaagcctcc aagcaaaatg   180
ctgtccagca tcttgggaaa gagcaacctc cagtttgcgg aatgagcat  ctctctgacc   240
atctccacgg ccagtctgaa cctgcgaact ccggactcca acagatcat  agcgaatcac   300
cacatgcggt ccatctcctt cgcctctggg ggagacccgg acacaactga ctatgttgca   360
tatgtggcta aggaccctgt taatcgcaga gcttgtcaca ttttggaatg ctgtgatggg   420
ctggcccagg atgtcatcgg ctccatcgga caagcctttg agctccggtt taagcaatat   480
ttacagtgtc ct                                                        492
```

<210> SEQ ID NO 5
<211> LENGTH: 96
<212> TYPE: PRT
<213> ORGANISM: Homo sapiens

<400> SEQUENCE: 5

```
             Trp Tyr Gln Gly Glu Met Ser Arg Lys Glu Ala Glu Gly Leu Leu Glu
             1               5                  10                  15

Lys Asp Gly Asp Phe Leu Val Arg Lys Ser Thr Thr Asn Pro Gly Ser
                         20                  25                  30

Phe Val Leu Thr Gly Met His Asn Gly Gln Ala Lys His Leu Leu Leu
                     35                  40                  45

Val Asp Pro Glu Gly Thr Ile Arg Thr Lys Asp Arg Val Phe Asp Ser
                 50                  55                  60

Ile Ser His Leu Ile Asn His His Leu Glu Ser Ser Leu Pro Ile Val
             65                  70                  75                  80
```

```
Ser Ala Gly Ser Glu Leu Cys Leu Gln Gln Pro Val Glu Arg Lys Gln
                85                  90                  95
```

<210> SEQ ID NO 6
<211> LENGTH: 288
<212> TYPE: DNA
<213> ORGANISM: Homo sapiens

<400> SEQUENCE: 6

```
tggtaccaag gagagatgag caggaaggag gcagaggggc tgctggagaa agacggagac      60
ttcctggtca ggaagagcac caccaacccg ggctcctttg tcctcacggg catgcacaat     120
ggccaggcca agcacctgct gctcgtggac ccagaaggca cgatccggac aaaggacaga     180
gtctttgaca gtatcagcca cctcatcaac caccacctag aaagcagcct gcccattgtc     240
tctgcaggga gtgagctgtg tctccagcag ccagtggaga ggaagcag                  288
```

<210> SEQ ID NO 7
<211> LENGTH: 594
<212> TYPE: PRT
<213> ORGANISM: Homo sapiens

<400> SEQUENCE: 7

```
Met Leu Pro Arg Thr Lys Tyr Asn Arg Phe Arg Asn Asp Ser Val Thr
 1               5                  10                  15

Ser Val Asp Asp Leu Leu His Ser Leu Ser Val Ser Gly Gly Gly Gly
                20                  25                  30

Lys Val Ser Ala Ala Arg Ala Thr Pro Ala Ala Ala Pro Tyr Leu Val
            35                  40                  45

Ser Gly Glu Ala Leu Arg Lys Ala Pro Asp Asp Pro Gly Ser Leu
        50                  55                  60

Gly His Leu Leu His Lys Val Ser His Leu Lys Leu Ser Ser Ser Gly
 65                  70                  75                  80

Leu Arg Gly Leu Ser Ser Ala Ala Arg Glu Arg Ala Gly Ala Arg Leu
                85                  90                  95

Ser Gly Ser Cys Ser Ala Pro Ser Leu Ala Ala Pro Asp Gly Ser Ala
                100                 105                 110

Pro Ser Ala His Arg Ala Pro Ala Met Ser Ala Ala Arg Lys Gly Arg
            115                 120                 125

Pro Gly Asp Glu Pro Leu Pro Arg Pro Pro Arg Gly Thr Pro His Ala
        130                 135                 140

Ser Asp Gln Val Leu Gly Pro Gly Val Thr Tyr Val Val Lys Tyr Leu
145                 150                 155                 160

Gly Cys Ile Glu Val Leu Arg Ser Met Arg Ser Leu Asp Phe Ser Thr
                165                 170                 175

Arg Thr Gln Ile Thr Arg Glu Ala Ile Ser Arg Val Cys Glu Ala Val
            180                 185                 190

Pro Gly Ala Lys Gly Ala Phe Lys Lys Arg Lys Pro Pro Ser Lys Met
        195                 200                 205

Leu Ser Ser Ile Leu Gly Lys Ser Asn Leu Gln Phe Ala Gly Met Ser
    210                 215                 220

Ile Ser Leu Thr Ile Ser Thr Ala Ser Leu Asn Leu Arg Thr Pro Asp
225                 230                 235                 240

Ser Lys Gln Ile Ile Ala Asn His His Met Arg Ser Ile Ser Phe Ala
                245                 250                 255

Ser Gly Gly Asp Pro Asp Thr Thr Asp Tyr Val Ala Tyr Val Ala Lys
```

```
                    260                 265                 270
Asp Pro Val Asn Arg Arg Ala Cys His Ile Leu Glu Cys Cys Asp Gly
                275                 280                 285
Leu Ala Gln Asp Val Ile Gly Ser Ile Gly Gln Ala Phe Glu Leu Arg
                290                 295                 300
Phe Lys Gln Tyr Leu Gln Cys Pro Thr Lys Ile Pro Ala Leu His Asp
305                 310                 315                 320
Arg Met Gln Ser Leu Asp Glu Pro Trp Thr Glu Glu Gly Asp Gly
                325                 330                 335
Ser Asp His Pro Tyr Tyr Asn Ser Ile Pro Ser Lys Met Pro Pro
                340                 345                 350
Gly Gly Phe Leu Asp Thr Arg Leu Lys Pro Arg Pro His Ala Pro Asp
                355                 360                 365
Thr Ala Gln Phe Ala Gly Lys Glu Gln Thr Tyr Tyr Gln Gly Arg His
                370                 375                 380
Leu Gly Asp Thr Phe Gly Glu Asp Trp Gln Gln Thr Pro Leu Arg Gln
385                 390                 395                 400
Gly Ser Ser Asp Ile Tyr Ser Thr Pro Glu Gly Lys Leu His Val Ala
                405                 410                 415
Pro Thr Gly Glu Ala Pro Thr Tyr Val Asn Thr Gln Ile Pro Pro
                420                 425                 430
Gln Ala Trp Pro Ala Ala Val Ser Ser Ala Glu Ser Ser Pro Arg Lys
                435                 440                 445
Asp Leu Phe Asp Met Lys Pro Phe Glu Asp Ala Leu Lys Asn Gln Pro
                450                 455                 460
Leu Gly Pro Val Leu Ser Lys Ala Ala Ser Val Glu Cys Ile Ser Pro
465                 470                 475                 480
Val Ser Pro Arg Ala Pro Asp Ala Lys Met Leu Glu Glu Leu Gln Ala
                485                 490                 495
Glu Thr Trp Tyr Gln Gly Glu Met Ser Arg Lys Glu Ala Glu Gly Leu
                500                 505                 510
Leu Glu Lys Asp Gly Asp Phe Leu Val Arg Lys Ser Thr Thr Asn Pro
                515                 520                 525
Gly Ser Phe Val Leu Thr Gly Met His Asn Gly Gln Ala Lys His Leu
                530                 535                 540
Leu Leu Val Asp Pro Glu Gly Thr Ile Arg Thr Lys Asp Arg Val Phe
545                 550                 555                 560
Asp Ser Ile Ser His Leu Ile Asn His His Leu Glu Ser Ser Leu Pro
                565                 570                 575
Ile Val Ser Ala Gly Ser Glu Leu Cys Leu Gln Pro Val Glu Arg
                580                 585                 590
Lys Gln

<210> SEQ ID NO 8
<211> LENGTH: 1785
<212> TYPE: DNA
<213> ORGANISM: Homo sapiens

<400> SEQUENCE: 8
atgcttccac gcaccaagta taaccgcttc aggaatgact cggtgacatc ggtcgatgac     60
cttctccaca gcctgtcggt gagcggcggc ggaggcaagg tttcggcggc gcgcgcgacc    120
ccggcggcgg ctccctactt ggtgtccggc gaggcgctgc gcaaggcgcc cgacgatggg    180
cccggcagcc tgggccacct gctccacaag gtgtcccacc tgaaactctc cagctcgggc    240
```

```
ctccgcggcc tgtcgtcggc cgcccgggag cgggcgggcg cgcggctctc gggcagctgc    300
agcgcgccca gcctggccgc cccggacggc agtgcgccct cggcgcaccg cgccccggcc    360
atgagcgccg ccaggaaggg ccggcccggc gacgagccgc tgcccaggcc ccctcggggg    420
acgccgcacg ccagcgacca ggtgctgggg cccggagtca cctacgtggt caagtacttg    480
gggtgcattg aagttctgcg ctcaatgagg tctcttgact tcagtacaag aacacaaatt    540
accagggaag ccatcagccg cgtctgtgaa gctgtgcctg gtgcgaaggg agccttcaag    600
aagagaaagc ctccaagcaa aatgctgtcc agcatcttgg gaaagagcaa cctccagttt    660
gcgggaatga gcatctctct gaccatctcc acggccagtc tgaacctgcg aactccggac    720
tccaaacaga tcatagcgaa tcaccacatg cggtccatct ccttcgcctc tgggggagac    780
ccggacacaa ctgactatgt tgcatatgtg gctaaggacc ctgttaatcg cagagcttgt    840
cacattttgg aatgctgtga tgggctggcc caggatgtca tcggctccat cggacaagcc    900
tttgagctcc ggtttaagca atatttacag tgtcctacca agattcccgc tctccatgat    960
cgaatgcaga gtctggatga gccatggacg gaagaggagg agatggctca gaccaccca   1020 tactacaaca gcatcccaag caagatgcct cctccagggg ctttcttga tactagactg    1080 aaacccagac cccatgctcc tgacacagcc cagtttgcag gaaaagagca gacttattac    1140
cagggaagac acttaggaga cacttttggc gaagactggc agcaaacacc tttaaggcaa    1200
gggtcctcgg acatctacag cacgccagaa gggaaactgc acgtggcccc cacgggagaa    1260
gcacccacct acgtcaacac tcagcagatc ccaccacagg cctggccggc tgcggtcagc    1320
agtgctgaga gcagcccgag gaaagacctc tttgacatga aaccttttga agatgctctc    1380
aagaaccagc ccttggggcc cgtgttaagc aaggcagcct ccgtggagtg catcagccct    1440
gtgtcaccta gagccccaga tgccaagatg ctggaggaac tgcaagccga gacttggtac    1500
caaggagaga tgagcaggaa ggaggcagag gggctgctgg agaaagacgg agacttcctg    1560
gtcaggaaga gcaccaccaa cccggggctcc tttgtcctca cgggcatgca caatggccag    1620
gccaagcacc tgctgctcgt ggacccagaa ggcacgatcg ggacaaagga cagagtcttt    1680
gacagtatca gccacctcat caaccaccac ctagaaagca gcctgcccat tgtctctgca    1740
gggagtgagc tgtgtctcca gcagccagtg gagaggaagc agtga              1785

<210> SEQ ID NO 9
<211> LENGTH: 422
<212> TYPE: DNA
<213> ORGANISM: Homo sapiens

<400> SEQUENCE: 9
ttgacttcag tacaagaaca caaattacca gggaagccat cagccgcgtc tgtgaagctg     60
tgcctggtgc gaagggagcc ttcaagaaga gaaagcctcc aagcaaaatg ctgtccagca    120
tcttgggaaa gagcaacctc cagtttgcgg gaatgagcat ctctctgacc atctccacgg    180
ccagtctgaa cctgcgaact ccggactcca aacagatcat agcgaatcac acatgcggt    240 ccatctcctt cgcctctggg ggagacccgg acacaactga ctatgttgca tatgtggcta    300
aggaccctgt taatcgcaga gcttgtcaca ttttggaatg ctgtgatggg ctggcccagg    360
atgtcatcgg ctccatcgga caagcctttg agctccggtt taagcaatat ttacagtgtc    420
ct                                                                     422

<210> SEQ ID NO 10
```

<211> LENGTH: 1425
<212> TYPE: DNA
<213> ORGANISM: Rattus sp.

<400> SEQUENCE: 10

| | | | | | |
|---|---|---|---|---|---|
| atgagcgcca | ccaggaagag | ccgggccagc | gacgagccgt | tgcccaggcc | ccgcggggc | 60 |
| gcgccgcacg | ccagcgacca | ggtgctgggg | tcgggagtca | cctatgtggt | caagtacttg | 120 |
| ggatgcatcg | aagttctgcg | ctcaatgagg | tctcttgact | tcagtacaag | aactcaggtt | 180 |
| accaggggaag | ccatcagccg | tgtctgcgaa | gctgtgccag | gcgccaaagg | agccttcaag | 240 |
| aagagaaagc | ctccgagtaa | aatgctgtcc | agcatcctgg | ggaagagcaa | cctccagttc | 300 |
| gcagggatga | gcatctccct | gaccatctcc | accgccagcc | tgaacctgcg | cactcctgac | 360 |
| tccaaacaga | tcatatcgaa | ccatcacatg | cggtccatct | ccttcgcctc | aggggagac | 420 |
| ccggacacaa | cagactatgt | tgcctacgtc | gctaaggacc | ctgtgaatcg | cagagcttgc | 480 |
| cacattctgg | aatgctgtga | cgggctagcc | caagatgtca | tcggctccat | cggacaagcc | 540 |
| tttgaactcc | ggttcaagca | gtatttgcag | tgtccttcca | agattcctgc | tctccaggac | 600 |
| cgaatgcaga | gtctggacga | gccgtggact | gaagaagagg | gagatggccc | cgatcacccg | 660 |
| tactacaaca | gcgttcccaa | caagatgcct | cctccaggag | ggtttctcga | tgctcgattg | 720 |
| aaagccagac | cccacgcacc | tgatgcagcc | cagttttcag | gaaaagagca | aacttattac | 780 |
| cagggaagac | acttaggaga | tgcattcggt | gaagactggc | agagagcacc | caccaggcaa | 840 |
| ggctccttgg | acatctatag | cacaccgaaa | gggaaagctc | acatggttcc | tgtaggagaa | 900 |
| acaccaacct | atgtcaacac | ccagccagtc | ccaccacagg | tttggccagc | agcaaccagc | 960 |
| agcactgaga | gcagcccacg | gaaggacctc | tttgacatga | gccttttga | agatgccctc | 1020 |
| agaaaccaac | ccctgggccc | tgtgttgagc | aaagctgcgt | ctgtggagtg | tatcagcccc | 1080 |
| gttacaccca | gagccccgga | cgccaagatg | ctggaggagc | ttaatgctga | gcctggtac | 1140 |
| caaggcgaga | tgagcaggaa | ggaggcagag | gctctactac | aggaagatgg | agacttccta | 1200 |
| gtcaggaaga | gtaccaccaa | ccccggctcc | tttgtcctca | caggcatgca | caatggccag | 1260 |
| gccaagcacc | tgctgctggt | ggacccggaa | ggcacggtcc | ggacgaagga | cagggtcttt | 1320 |
| gacagcatca | gtcacctcat | tacttaccac | ctggagagca | gcctgcccat | tgtctctgcc | 1380 |
| gggagtgagc | tttgtctccg | gcaaccagtg | gagaggaaac | cctga | | 1425 |

<210> SEQ ID NO 11
<211> LENGTH: 474
<212> TYPE: PRT
<213> ORGANISM: Rattus sp.

<400> SEQUENCE: 11

Met Ser Ala Thr Arg Lys Ser Arg Ala Ser Asp Glu Pro Leu Pro Arg
1               5                   10                  15

Pro Pro Arg Gly Ala Pro His Ala Ser Asp Gln Val Leu Gly Ser Gly
                20                  25                  30

Val Thr Tyr Val Val Lys Tyr Leu Gly Cys Ile Glu Val Leu Arg Ser
            35                  40                  45

Met Arg Ser Leu Asp Phe Ser Thr Arg Thr Gln Val Thr Arg Glu Ala
        50                  55                  60

Ile Ser Arg Val Cys Glu Ala Val Pro Gly Ala Lys Gly Ala Phe Lys
65                  70                  75                  80

Lys Arg Lys Pro Pro Ser Lys Met Leu Ser Ser Ile Leu Gly Lys Ser
                85                  90                  95

```
Asn Leu Gln Phe Ala Gly Met Ser Ile Ser Leu Thr Ile Ser Thr Ala
            100                 105                 110
Ser Leu Asn Leu Arg Thr Pro Asp Ser Lys Gln Ile Ile Ser Asn His
        115                 120                 125
His Met Arg Ser Ile Ser Phe Ala Ser Gly Gly Asp Pro Asp Thr Thr
    130                 135                 140
Asp Tyr Val Ala Tyr Val Ala Lys Asp Pro Val Asn Arg Arg Ala Cys
145                 150                 155                 160
His Ile Leu Glu Cys Cys Asp Gly Leu Ala Gln Asp Val Ile Gly Ser
                165                 170                 175
Ile Gly Gln Ala Phe Glu Leu Arg Phe Lys Gln Tyr Leu Gln Cys Pro
            180                 185                 190
Ser Lys Ile Pro Ala Leu Gln Asp Arg Met Gln Ser Leu Asp Glu Pro
        195                 200                 205
Trp Thr Glu Glu Glu Gly Asp Gly Pro Asp His Pro Tyr Tyr Asn Ser
    210                 215                 220
Val Pro Asn Lys Met Pro Pro Gly Gly Phe Leu Asp Ala Arg Leu
225                 230                 235                 240
Lys Ala Arg Pro His Ala Pro Asp Ala Ala Gln Phe Ser Gly Lys Glu
                245                 250                 255
Gln Thr Tyr Tyr Gln Gly Arg His Leu Gly Asp Ala Phe Gly Glu Asp
            260                 265                 270
Trp Gln Arg Ala Pro Thr Arg Gln Gly Ser Leu Asp Ile Tyr Ser Thr
        275                 280                 285
Pro Glu Gly Lys Ala His Met Val Pro Val Gly Glu Thr Pro Thr Tyr
    290                 295                 300
Val Asn Thr Gln Pro Val Pro Pro Gln Val Trp Pro Ala Ala Thr Ser
305                 310                 315                 320
Ser Thr Glu Ser Ser Pro Arg Lys Asp Leu Phe Asp Met Lys Pro Phe
                325                 330                 335
Glu Asp Ala Leu Arg Asn Gln Pro Leu Gly Pro Val Leu Ser Lys Ala
            340                 345                 350
Ala Ser Val Glu Cys Ile Ser Pro Val Thr Pro Arg Ala Pro Asp Ala
        355                 360                 365
Lys Met Leu Glu Glu Leu Asn Ala Glu Pro Trp Tyr Gln Gly Glu Met
    370                 375                 380
Ser Arg Lys Glu Ala Glu Ala Leu Leu Gln Glu Asp Gly Asp Phe Leu
385                 390                 395                 400
Val Arg Lys Ser Thr Thr Asn Pro Gly Ser Phe Val Leu Thr Gly Met
                405                 410                 415
His Asn Gly Gln Ala Lys His Leu Leu Leu Val Asp Pro Glu Gly Thr
            420                 425                 430
Val Arg Thr Lys Asp Arg Val Phe Asp Ser Ile Ser His Leu Ile Thr
        435                 440                 445
Tyr His Leu Glu Ser Ser Leu Pro Ile Val Ser Ala Gly Ser Glu Leu
    450                 455                 460
Cys Leu Arg Gln Pro Val Glu Arg Lys Pro
465                 470

<210> SEQ ID NO 12
<211> LENGTH: 492
<212> TYPE: DNA
<213> ORGANISM: Rattus sp.
```

-continued

```
<400> SEQUENCE: 12
ctggggtcgg gagtcaccta tgtggtcaag tacttgggat gcatcgaagt tctgcgctca      60
atgaggtctc ttgacttcag tacaagaact caggttacca gggaagccat cagccgtgtc     120
tgcgaagctg tgccaggcgc aaaggagcc ttcaagaaga gaaagcctcc gagtaaaatg      180
ctgtccagca tcctggggaa gagcaacctc cagttcgcag ggatgagcat ctccctgacc     240
atctccaccg ccagcctgaa cctgcgcact cctgactcca acagatcat atcgaaccat      300 cacatgcggt ccatctcctt cgcctcaggg ggagacccgg acacaacaga ctatgttgcc     360
tacgtcgcta aggaccctgt gaatcgcaga gcttgccaca ttctggaatg ctgtgacggg     420
ctagcccaag atgtcatcgg ctccatcgga caagcctttg aactccggtt caagcagtat     480
ttgcagtgtc ct                                                         492

<210> SEQ ID NO 13
<211> LENGTH: 164
<212> TYPE: PRT
<213> ORGANISM: Rattus sp.

<400> SEQUENCE: 13

Leu Gly Ser Gly Val Thr Tyr Val Val Lys Tyr Leu Gly Cys Ile Glu
  1               5                  10                  15

Val Leu Arg Ser Met Arg Ser Leu Asp Phe Ser Thr Arg Thr Gln Val
             20                  25                  30

Thr Arg Glu Ala Ile Ser Arg Val Cys Glu Ala Val Pro Gly Ala Lys
         35                  40                  45

Gly Ala Phe Lys Lys Arg Lys Pro Ser Lys Met Leu Ser Ser Ile
     50                  55                  60

Leu Gly Lys Ser Asn Leu Gln Phe Ala Gly Met Ser Ile Ser Leu Thr
 65                  70                  75                  80

Ile Ser Thr Ala Ser Leu Asn Leu Arg Thr Pro Asp Ser Lys Gln Ile
                 85                  90                  95

Ile Ser Asn His His Met Arg Ser Ile Ser Phe Ala Ser Gly Gly Asp
            100                 105                 110

Pro Asp Thr Thr Asp Tyr Val Ala Tyr Val Ala Lys Asp Pro Val Asn
        115                 120                 125

Arg Arg Ala Cys His Ile Leu Glu Cys Cys Asp Gly Leu Ala Gln Asp
    130                 135                 140

Val Ile Gly Ser Ile Gly Gln Ala Phe Glu Leu Arg Phe Lys Gln Tyr
145                 150                 155                 160

Leu Gln Cys Pro

<210> SEQ ID NO 14
<211> LENGTH: 288
<212> TYPE: DNA
<213> ORGANISM: Rattus sp.

<400> SEQUENCE: 14
tggtaccaag gcgagatgag caggaaggag gcagaggctc tactacagga agatggagac      60
ttcctagtca ggaagagtac caccaacccc ggctcctttg tcctcacagg catgcacaat     120
ggccaggcca agcacctgct gctggtggac ccggaaggca cggtccggac gaaggacagg     180
gtctttgaca gcatcagtca cctcattact taccacctgg agagcagcct gcccattgtc     240
tctgccggga gtgagctttg tctccggcaa ccagtggaga ggaaaccc                  288
```

-continued

<210> SEQ ID NO 15
<211> LENGTH: 96
<212> TYPE: PRT
<213> ORGANISM: Rattus sp.

<400> SEQUENCE: 15

```
Trp Tyr Gln Gly Glu Met Ser Arg Lys Glu Ala Glu Ala Leu Leu Gln
  1               5                  10                  15

Glu Asp Gly Asp Phe Leu Val Arg Lys Ser Thr Thr Asn Pro Gly Ser
             20                  25                  30

Phe Val Leu Thr Gly Met His Asn Gly Gln Ala Lys His Leu Leu Leu
         35                  40                  45

Val Asp Pro Glu Gly Thr Val Arg Thr Lys Asp Arg Val Phe Asp Ser
     50                  55                  60

Ile Ser His Leu Ile Thr Tyr His Leu Glu Ser Ser Leu Pro Ile Val
 65                  70                  75                  80

Ser Ala Gly Ser Glu Leu Cys Leu Arg Gln Pro Val Glu Arg Lys Pro
                 85                  90                  95
```

<210> SEQ ID NO 16
<211> LENGTH: 1785
<212> TYPE: DNA
<213> ORGANISM: Rattus sp.

<400> SEQUENCE: 16

| | |
|---|---|
| atgcttccac gcaccaagta caaccgcttc aggaatgact cggtgacatc ggtcgatgac | 60 |
| cttctccaca gcctgtcggt gagcggcagc ggcggcaagg tctcggcgga gcccgcggcg | 120 |
| agcccctacc tggtgtcggg cgaggcgctg cgcaaggcgc cggacgatgg gcccggcagc | 180 |
| ctgggccacc tgctccacaa ggtgtcccac ttgaaactct ccagctccgg cctgcgtggc | 240 |
| ctgtcgtcgg ccgcccggga gcgggcagga gcgcggctct cgggcagctg cagcgcgccc | 300 |
| agcctggcgg ccccggacgg tggcagcgcg accccggggt cccgtgcccc ggccgccagc | 360 |
| atgagcgcca ccaggaagag ccgggccagc gacgagccgt tgcccaggcc ccgcggggc | 420 |
| gcgccgcacg ccagcgacca ggtgctgggg tcgggagtca cctatgtggt caagtacttg | 480 |
| ggatgcatcg aagttctgcg ctcaatgagg tctcttgact tcagtacaag aactcaggtt | 540 |
| accagggaag ccatcagccg tgtctgcgaa gctgtgccag gcgccaaagg agccttcaag | 600 |
| aagagaaagc ctccgagtaa aatgctgtcc agcatcctgg ggaagagcaa cctccagttc | 660 |
| gcagggatga gcatctccct gaccatctcc accgccagcc tgaacctgcg cactcctgac | 720 |
| tccaaacaga tcatatcgaa ccatcacatg cggtccatct ccttcgcctc agggggagac | 780 |
| ccggacacaa cagactatgt tgcctacgtc gctaaggacc ctgtgaatcg cagagcttgc | 840 |
| cacattctgg aatgctgtga cgggctagcc caagatgtca tcggctccat cggacaagcc | 900 |
| tttgaactcc ggttcaagca gtatttgcag tgtccttcca agattcctgc tctccaggac | 960 |
| cgaatgcaga gtctggacga gccgtggact gaagaagagg gagatggccc cgatcacccg | 1020 |
| tactacaaca gcgttcccaa caagatgcct cctccaggag ggtttctcga tgctcgattg | 1080 |
| aaagccagac cccacgcacc tgatgcagcc cagttttcag gaaaagagca aacttattac | 1140 |
| cagggaagac acttaggaga tgcattcggt gaagactggc agagagcacc caccaggcaa | 1200 |
| ggctccttgg acatctatag cacaccagaa gggaaagctc acatggttcc tgtaggagaa | 1260 |
| acaccaacct atgtcaacac ccagccagtc ccaccacagg tttggccagc agcaaccagc | 1320 |
| agcactgaga gcagcccacg gaaggacctc tttgacatga agccttttga agatgccctc | 1380 |

```
agaaaccaac ccctgggccc tgtgttgagc aaagctgcgt ctgtggagtg tatcagcccc    1440
gttacaccca gagccccgga cgccaagatg ctggaggagc ttaatgctga gccctggtac    1500
caaggcgaga tgagcaggaa ggaggcagag gctctactac aggaagatgg agacttccta    1560
gtcaggaaga gtaccaccaa ccccggctcc tttgtcctca caggcatgca caatggccag    1620
gccaagcacc tgctgctggt ggacccggaa ggcacggtcc ggacgaagga cagggtcttt    1680
gacagcatca gtcacctcat tacttaccac ctggagagca gcctgcccat tgtctctgcc    1740
gggagtgagc tttgtctccg gcaaccagtg gagaggaaac cctga                    1785
```

<210> SEQ ID NO 17
<211> LENGTH: 594
<212> TYPE: PRT
<213> ORGANISM: Rattus sp.

<400> SEQUENCE: 17

```
Met Leu Pro Arg Thr Lys Tyr Asn Arg Phe Arg Asn Asp Ser Val Thr
 1               5                   10                  15

Ser Val Asp Asp Leu Leu His Ser Leu Ser Val Ser Gly Ser Gly Gly
            20                  25                  30

Lys Val Ser Ala Glu Pro Ala Ala Ser Pro Tyr Leu Val Ser Gly Glu
        35                  40                  45

Ala Leu Arg Lys Ala Pro Asp Asp Gly Pro Gly Ser Leu Gly His Leu
    50                  55                  60

Leu His Lys Val Ser His Leu Lys Leu Ser Ser Gly Leu Arg Gly
65                  70                  75                  80

Leu Ser Ser Ala Ala Arg Glu Arg Ala Gly Ala Arg Leu Ser Gly Ser
                85                  90                  95

Cys Ser Ala Pro Ser Leu Ala Ala Pro Asp Gly Gly Ser Ala Thr Pro
            100                 105                 110

Gly Ser Arg Ala Pro Ala Ala Ser Met Ser Ala Thr Arg Lys Ser Arg
        115                 120                 125

Ala Ser Asp Glu Pro Leu Pro Arg Pro Pro Arg Gly Ala Pro His Ala
    130                 135                 140

Ser Asp Gln Val Leu Gly Ser Gly Val Thr Tyr Val Val Lys Tyr Leu
145                 150                 155                 160

Gly Cys Ile Glu Val Leu Arg Ser Met Arg Ser Leu Asp Phe Ser Thr
                165                 170                 175

Arg Thr Gln Val Thr Arg Glu Ala Ile Ser Arg Val Cys Glu Ala Val
            180                 185                 190

Pro Gly Ala Lys Gly Ala Phe Lys Lys Arg Lys Pro Pro Ser Lys Met
        195                 200                 205

Leu Ser Ser Ile Leu Gly Lys Ser Asn Leu Gln Phe Ala Gly Met Ser
    210                 215                 220

Ile Ser Leu Thr Ile Ser Thr Ala Ser Leu Asn Leu Arg Thr Pro Asp
225                 230                 235                 240

Ser Lys Gln Ile Ile Ser Asn His His Met Arg Ser Ile Ser Phe Ala
                245                 250                 255

Ser Gly Gly Asp Pro Asp Thr Thr Asp Tyr Val Ala Tyr Val Ala Lys
            260                 265                 270

Asp Pro Val Asn Arg Arg Ala Cys His Ile Leu Glu Cys Cys Asp Gly
        275                 280                 285

Leu Ala Gln Asp Val Ile Gly Ser Ile Gly Gln Ala Phe Glu Leu Arg
    290                 295                 300
```

```
Phe Lys Gln Tyr Leu Gln Cys Pro Ser Lys Ile Pro Ala Leu Gln Asp
305                 310                 315                 320

Arg Met Gln Ser Leu Asp Glu Pro Trp Thr Glu Glu Gly Asp Gly
                325                 330                 335

Pro Asp His Pro Tyr Tyr Asn Ser Val Pro Asn Lys Met Pro Pro
            340                 345                 350

Gly Gly Phe Leu Asp Ala Arg Leu Lys Ala Arg Pro His Ala Pro Asp
            355                 360                 365

Ala Ala Gln Phe Ser Gly Lys Glu Gln Thr Tyr Tyr Gln Gly Arg His
            370                 375                 380

Leu Gly Asp Ala Phe Gly Glu Asp Trp Gln Arg Ala Pro Thr Arg Gln
385                 390                 395                 400

Gly Ser Leu Asp Ile Tyr Ser Thr Pro Glu Gly Lys Ala His Met Val
                405                 410                 415

Pro Val Gly Glu Thr Pro Thr Tyr Val Asn Thr Gln Pro Val Pro Pro
            420                 425                 430

Gln Val Trp Pro Ala Ala Thr Ser Thr Glu Ser Ser Pro Arg Lys
            435                 440                 445

Asp Leu Phe Asp Met Lys Pro Phe Glu Asp Ala Leu Arg Asn Gln Pro
            450                 455                 460

Leu Gly Pro Val Leu Ser Lys Ala Ala Ser Val Glu Cys Ile Ser Pro
465                 470                 475                 480

Val Thr Pro Arg Ala Pro Asp Ala Lys Met Leu Glu Leu Asn Ala
                485                 490                 495

Glu Pro Trp Tyr Gln Gly Glu Met Ser Arg Lys Glu Ala Glu Ala Leu
                500                 505                 510

Leu Gln Glu Asp Gly Asp Phe Leu Val Arg Lys Ser Thr Thr Asn Pro
            515                 520                 525

Gly Ser Phe Val Leu Thr Gly Met His Asn Gly Gln Ala Lys His Leu
            530                 535                 540

Leu Leu Val Asp Pro Glu Gly Thr Val Arg Thr Lys Asp Arg Val Phe
545                 550                 555                 560

Asp Ser Ile Ser His Leu Ile Thr Tyr His Leu Glu Ser Ser Leu Pro
                565                 570                 575

Ile Val Ser Ala Gly Ser Glu Leu Cys Leu Arg Gln Pro Val Glu Arg
                580                 585                 590

Lys Pro

<210> SEQ ID NO 18
<211> LENGTH: 16
<212> TYPE: PRT
<213> ORGANISM: Homo sapiens

<400> SEQUENCE: 18

Pro Trp Thr Glu Glu Gly Asp Gly Ser Asp His Pro Tyr Tyr Asn
1               5                   10                  15

<210> SEQ ID NO 19
<211> LENGTH: 15
<212> TYPE: PRT
<213> ORGANISM: Homo sapiens

<400> SEQUENCE: 19

Gln Thr Pro Leu Arg Gln Gly Ser Ser Asp Ile Tyr Ser Thr Pro
1               5                   10                  15
```

```
<210> SEQ ID NO 20
<211> LENGTH: 11
<212> TYPE: PRT
<213> ORGANISM: Unknown Organism
<220> FEATURE:
<223> OTHER INFORMATION: Description of Unknown Organism: T7 phage

<400> SEQUENCE: 20

Met Ala Ser Met Thr Gly Gly Gln Gln Met Gly
 1               5                  10

<210> SEQ ID NO 21
<211> LENGTH: 164
<212> TYPE: PRT
<213> ORGANISM: Homo sapiens

<400> SEQUENCE: 21

Leu Gly Pro Gly Val Thr Tyr Val Val Lys Tyr Leu Gly Cys Ile Glu
 1               5                  10                  15

Val Leu Arg Ser Met Arg Ser Leu Asp Phe Ser Thr Arg Thr Gln Ile
            20                  25                  30

Thr Arg Glu Ala Ile Ser Arg Val Cys Glu Ala Val Pro Gly Ala Lys
        35                  40                  45

Gly Ala Phe Lys Lys Arg Lys Pro Pro Ser Lys Met Leu Ser Ser Ile
    50                  55                  60

Leu Gly Lys Ser Asn Leu Gln Phe Ala Gly Met Ser Ile Ser Leu Thr
65                  70                  75                  80

Ile Ser Thr Ala Ser Leu Asn Leu Arg Thr Pro Asp Ser Lys Gln Ile
                85                  90                  95

Ile Ala Asn His His Met Arg Ser Ile Ser Phe Ala Ser Gly Gly Asp
            100                 105                 110

Pro Asp Thr Thr Asp Tyr Val Ala Tyr Val Ala Lys Asp Pro Val Asn
        115                 120                 125

Arg Arg Ala Cys His Ile Leu Glu Cys Cys Asp Gly Leu Ala Gln Asp
    130                 135                 140

Val Ile Gly Ser Ile Gly Gln Ala Phe Glu Leu Arg Phe Lys Gln Tyr
145                 150                 155                 160

Leu Gln Cys Pro

<210> SEQ ID NO 22
<211> LENGTH: 164
<212> TYPE: PRT
<213> ORGANISM: Homo sapiens

<400> SEQUENCE: 22

Met Gly Pro Gly Val Ser Tyr Leu Val Arg Tyr Met Gly Cys Val Glu
 1               5                  10                  15

Val Leu Gln Ser Met Arg Ala Leu Asp Phe Asn Thr Arg Thr Gln Val
            20                  25                  30

Thr Arg Glu Ala Ile Ser Leu Val Cys Glu Ala Val Pro Gly Ala Lys
        35                  40                  45

Gly Ala Thr Arg Arg Arg Lys Pro Cys Ser Arg Pro Leu Ser Ser Ile
    50                  55                  60

Leu Gly Arg Ser Asn Leu Lys Phe Ala Gly Met Pro Ile Thr Leu Thr
65                  70                  75                  80

Val Ser Thr Ser Ser Leu Asn Leu Met Ala Ala Asp Cys Lys Gln Ile
                85                  90                  95

Ile Ala Asn His His Met Gln Ser Ile Ser Phe Ala Ser Gly Gly Asp
```

-continued

```
                100                 105                 110
Pro Asp Thr Ala Glu Tyr Val Ala Tyr Val Ala Lys Asp Pro Val Asn
                115                 120                 125
Gln Arg Ala Cys His Ile Leu Glu Cys Pro Gly Leu Ala Gln Asp
        130                 135                 140
Val Ile Ser Thr Ile Gly Gln Ala Phe Glu Leu Arg Phe Lys Gln Tyr
145                 150                 155                 160
Leu Arg Asn Pro

<210> SEQ ID NO 23
<211> LENGTH: 96
<212> TYPE: PRT
<213> ORGANISM: Homo sapiens

<400> SEQUENCE: 23

Trp Tyr Gln Gly Glu Met Ser Arg Lys Glu Ala Glu Gly Leu Leu Glu
  1               5                  10                  15
Lys Asp Gly Asp Phe Leu Val Arg Lys Ser Thr Thr Asn Pro Gly Ser
                20                  25                  30
Phe Val Leu Thr Gly Met His Asn Gly Gln Ala Lys His Leu Leu Leu
            35                  40                  45
Val Asp Pro Glu Gly Thr Ile Arg Thr Lys Asp Arg Val Phe Asp Ser
 50                  55                  60
Ile Ser His Leu Ile Asn His His Leu Glu Ser Ser Leu Pro Ile Val
 65                  70                  75                  80
Ser Ala Gly Ser Glu Leu Cys Leu Gln Gln Pro Val Glu Arg Lys Gln
                85                  90                  95

<210> SEQ ID NO 24
<211> LENGTH: 96
<212> TYPE: PRT
<213> ORGANISM: Homo sapiens

<400> SEQUENCE: 24

Trp Phe His Gly Lys Leu Ser Arg Arg Glu Ala Glu Ala Leu Leu Gln
  1               5                  10                  15
Leu Asn Gly Asp Phe Leu Val Arg Glu Ser Thr Thr Thr Pro Gly Gln
                20                  25                  30
Tyr Val Leu Thr Gly Leu Gln Ser Gly Gln Pro Lys His Leu Leu Leu
            35                  40                  45
Val Asp Pro Glu Gly Val Val Arg Thr Lys Asp His Arg Phe Glu Ser
 50                  55                  60
Val Ser His Leu Ile Ser Tyr His Met Asp Asn His Leu Pro Ile Ile
 65                  70                  75                  80
Ser Ala Gly Ser Glu Leu Cys Leu Gln Gln Pro Val Glu Arg Lys Leu
                85                  90                  95
```

What is claimed is:

1. An isolated polynucleotide comprising the sequence as set forth in SEQ ID NO: 8.

2. An isolated polynucleotide encoding the polypeptide having the amino acid sequence as set forth in SEQ ID NO: 7.

3. An isolated polynucleotide encoding the polypeptide having the amino acid sequence as set forth in SEQ ID NO: 1.

4. An isolated polynucleotide encoding the polypeptide having the amino acid sequence as set forth in SEQ ID NO: 3.

5. An isolated polynucleotide encoding the polypeptide having the amino acid sequence as set forth in SEQ ID NO: 5.

* * * * *